(12) United States Patent
Sakai et al.

(10) Patent No.: US 11,529,819 B2
(45) Date of Patent: Dec. 20, 2022

(54) RECORDING MATERIAL AND COMPOUND

(71) Applicant: NIPPON SODA CO., LTD., Tokyo (JP)

(72) Inventors: Hiroshi Sakai, Ichihara (JP); Kayoko Tada, Ichihara (JP); Shuntaro Kinoshita, Ichihara (JP)

(73) Assignee: NIPPON SODA CO., LTD., Tokyo (JP)

( * ) Notice: Subject to any disclaimer, the term of this patent is extended or adjusted under 35 U.S.C. 154(b) by 467 days.

(21) Appl. No.: 16/617,442

(22) PCT Filed: Jun. 1, 2018

(86) PCT No.: PCT/JP2018/021290
§ 371 (c)(1),
(2) Date: Nov. 26, 2019

(87) PCT Pub. No.: WO2018/225663
PCT Pub. Date: Dec. 13, 2018

(65) Prior Publication Data
US 2020/0086669 A1      Mar. 19, 2020

(30) Foreign Application Priority Data

Jun. 8, 2017 (JP) .............................. JP2017-113439

(51) Int. Cl.

| | | |
|---|---|---|
| B41M 5/333 | (2006.01) | |
| B41M 5/155 | (2006.01) | |
| C07C 275/34 | (2006.01) | |
| C07C 309/73 | (2006.01) | |
| B41M 5/327 | (2006.01) | |

(52) U.S. Cl.
CPC .......... *B41M 5/3333* (2013.01); *B41M 5/155* (2013.01); *C07C 275/34* (2013.01); *C07C 309/73* (2013.01); *B41M 5/3275* (2013.01); *B41M 5/3335* (2013.01); *B41M 2205/04* (2013.01); *B41M 2205/28* (2013.01)

(58) Field of Classification Search
CPC .. B41M 5/155; B41M 5/3333; B41M 5/3335; B41M 5/3336; B41M 5/3375; B41M 2205/04; B41M 2205/28
See application file for complete search history.

(56) References Cited

U.S. PATENT DOCUMENTS

| | | |
|---|---|---|
| 5,041,605 A | 8/1991 | Huson et al. |
| 6,291,619 B1 | 9/2001 | Maekawa et al. |
| 10,780,724 B2 * | 9/2020 | Miyanaga ............ B41M 5/3335 |
| 2005/0267119 A1 | 12/2005 | Chao et al. |
| 2009/0023731 A1 | 1/2009 | Gless, Jr. et al. |
| 2011/0065734 A1 | 3/2011 | Bar et al. |
| 2015/0284321 A1 | 10/2015 | Sakai et al. |
| 2015/0367663 A1 | 12/2015 | Yamane et al. |
| 2016/0137595 A1 | 5/2016 | Markwalder et al. |
| 2018/0345710 A1 | 12/2018 | Miyanaga et al. |

FOREIGN PATENT DOCUMENTS

| | | |
|---|---|---|
| EP | 1 116713 A1 | 7/2001 |
| EP | 2 060 565 A1 | 5/2009 |
| GB | 2 441 020 A | 2/2008 |
| JP | H03-174536 A | 7/1991 |
| JP | H08-002111 A | 1/1996 |
| JP | H08-002112 A | 1/1996 |
| JP | H09-227495 A | 9/1997 |
| JP | H11-268421 A | 10/1999 |
| JP | 2011-184407 A | 9/2011 |
| JP | 2017-165091 A | 9/2017 |
| WO | 98/034159 A1 | 8/1998 |
| WO | 00/14058 A1 | 3/2000 |
| WO | 2005/113511 A1 | 12/2005 |
| WO | 2014/080615 A1 | 5/2014 |
| WO | 2015/002918 A1 | 1/2015 |
| WO | 2017/111032 A1 | 6/2017 |

OTHER PUBLICATIONS

Nov. 22, 2021 Office Action issued in Indian Patent Application No. 201947049611.
Kim et al., "Pyridyl-urea Derivatives as Blockers of Aβ-induced mPTP Opening for Alzheimer's Disease," Bull. Korean Chem. Soc., 2012, vol. 33, No. 11, pp. 3887-3888.
Senda et al., "Uracil Derivatives and Related Compounds. VII. Synthesis and Anti-inflammatory Activity of Bucolome's Related Compounds," Journal of the Pharmaceutical Society of Japan, 1969, vol. 89, pp. 254-259.
Eissa et al., "Diphenylurea derivatives for combating methicillin- and vancomycin- resistant *Staphylococcus aureus*," European Journal of Medicinal Chemistry, 2017, vol. 130, pp. 73-85.

(Continued)

*Primary Examiner* — Gerard Higgins
(74) *Attorney, Agent, or Firm* — Oliff PLC

(57) ABSTRACT

An object of the present invention is to provide a recording material or a recording sheet using, as a color-developing agent, a non-phenol-based compound good in color developing performance and the like. A compound represented by the following formula (I) is used as the color-developing agent:

(I)

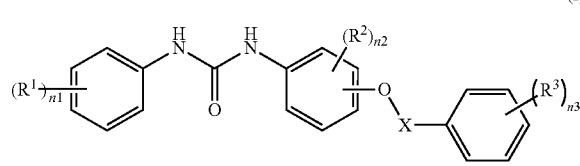

(wherein X represents $CH_2$ or the like; $R^1$ to $R^3$ each independently represent a hydrogen atom, a halogen atom or the like; n1 and n3 each independently represent any integer of 1 to 5; two groups represented by $R^3$ adjacent to each other on a benzene ring optionally bond to each other to form an optionally substituted 6-membered ring; and n2 represents any integer of 1 to 4).

2 Claims, No Drawings

(56) References Cited

OTHER PUBLICATIONS

Feb. 9, 2021 Extended Search Report issued in European Patent Application No. 18813434.0.
Konovalova et al., "Reaction of N-Arylcarbamoyl-1,4-benzoquinone Imines with Sodium Arenesulfinates," Russian Journal of Organic Chemistry, 2014, vol. 50, No. 9, pp. 1292-1300.
Gwaltney et al., "Novel sulfonate Derivatives: potent antimitotic agents," Bioorganic & Medicinal Chemistry Letters, Jul. 9, 2001, vol. 11, No. 13, pp. 1671-1673.
Raiford et al., "Migration of the Carbamyl Radical in 2-Aminophenol Derivatives," J. Org. Chem., 1940, vol. 5, No. 3, pp. 300-312.
Apr. 3, 2008 Office Action issued in Taiwanese Patent Application No. 107119446.
Jul. 17, 2018 International Search Report issued in International Patent Application No. PCT/JP2018/021290.

* cited by examiner

RECORDING MATERIAL AND COMPOUND

TECHNICAL FIELD

The present invention relates to a thermal or pressure-sensitive recording material employing color development through a reaction between a color former and a color-developing agent.

The present application claims priority based on Japanese Patent Application No. 2017-113439 filed on Jun. 8, 2017, and the contents thereof are incorporated herein by reference in their entirety.

BACKGROUND ART

Recording materials that employ color development through a reaction between a color former and a color-developing agent allow recording in a short time using a relatively simple apparatus without performing complicated treatments such as development and fixation and are thus widely used in thermal recording paper for output recording in facsimiles, printers, etc., or pressure-sensitive copying paper or the like for forms for simultaneous multiple copying. These recording materials are required to immediately develop colors, maintain the whiteness of an uncolored part (hereinafter, referred to as a "background"), and offer high colorfastness of colored images. For this purpose, attempts have been made to develop color former, color-developing agents, storage stabilizers, etc. Nevertheless, few recording materials have well-balanced, sufficiently satisfactory color-developing sensitivity, background and image storage property, etc.

On the other hand, although a phenol color-developing agent such as 4,4'-isopropylidene diphenol shows good color-developing performance, such an agent can correspond to an endocrine disruptor and is not allowed to be used for some users. Therefore, a color-developing agent having a structure not containing a phenol skeleton (which is hereinafter referred to as the non-phenol-based) is required.

A non-phenol-based color-developing agent having a diphenylurea structure has already been known. Although diphenylurea itself (see Patent Document 1) has a problem in color developing performance, as a related compound improved in the performance as a color-developing agent, a urea-urethane compound described in Patent Document 2, a compound having a diphenylurea structure and a sulfonamide structure described in Patent Document 3 or 4 or the like may be exemplified.

Besides, as a related compound, those described in Patent Document 5 and Non-patent Documents 1 to 3 may be exemplified, which are known for use in a pharmaceutical (an antiatherosclerotic agent or an antimitotic agent) but not known for use in a recording material.

The present inventors have further searched for a non-phenol-based color-developing agent excellent in color developing performance.

PRIOR ART DOCUMENTS

Patent Documents

Patent Document 1: Japanese unexamined Patent Application Publication No. 8-2112
Patent Document 2: International Publication No. WO00/14058
Patent Document 3: Japanese unexamined Patent Application Publication No. 11-268421
Patent Document 4: International Publication No. WO2014-080615
Patent Document 5: Japanese unexamined Patent Application Publication No. 9-227495

Non-Patent Documents

Non-patent Document 1: Russian J. Org. Chem., September 2014, 50, 9, 1292-1300 Non-patent Document 2: Bioorg. Med. Chem. Lett., 9 Jul. 2001, 11, 13, 1671-1673 Non-patent Document 3: J. Org. Chem., 1940, 05(3), 300-312

SUMMARY OF THE INVENTION

Object to be Solved by the Invention

An object of the present invention is to provide a recording material or a recording sheet using, as a color-developing agent, a non-phenol-based compound good in color-developing performance, etc.

Means to Solve the Object

The present inventors have found a compound having a non-phenol-based structure and good in color developing performance and the like, resulting in accomplishing the present invention.

Specifically, the present invention relates to the following inventions:

(1) A recording material containing a color former, wherein the recording material contains at least one compound selected from the group consisting of compounds represented by the following formula (I):

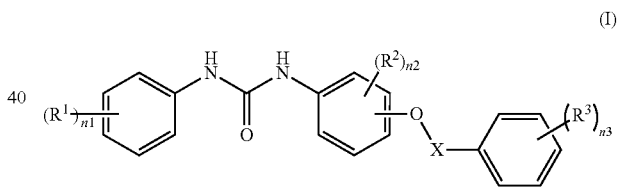

(wherein X represents $CH_2$, C=O, or $SO_2$;
$R^1$ to $R^3$ each independently represent a hydrogen atom, a halogen atom, a nitro group, a cyano group, a linear, branched or cyclic C1-C6 alkylcarbonyl group, a linear, branched or cyclic C1-C6 alkyl group, a linear, branched or cyclic C1-C6 alkoxy group, a C2-C6 alkenyl group, a linear, branched or cyclic C1-C6 fluoroalkyl group, a $N(R^4)_2$ group (wherein $R^4$ represents a hydrogen atom, a phenyl group, a benzyl group, or a linear, branched or cyclic C1-C6 alkyl group), a $NHCOR^5$ group (wherein $R^5$ represents a linear, branched or cyclic C1-C6 alkyl group), an optionally substituted phenyl group, or an optionally substituted benzyl group;
n1 and n3 each independently represent any integer of 1 to 5;
two groups represented by $R^3$ adjacent to each other on a benzene ring optionally bond to each other to form an optionally substituted 6-membered ring; and n2 represents any integer of 1 to 4).

(2) A recording sheet having a recording material layer formed with the recording material according to (1) on a support.

(3) A method for using, as a color-developing agent, at least one compound selected from the group consisting of compounds represented by the following formula (I):

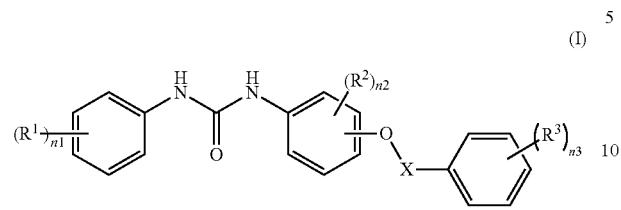

(wherein X represents $CH_2$, $C=O$, or $SO_2$;
$R^1$ to $R^3$ each independently represent a hydrogen atom, a halogen atom, a nitro group, a cyano group, a linear, branched or cyclic C1-C6 alkylcarbonyl group, a linear, branched or cyclic C1-C6 alkyl group, a linear, branched or cyclic C1-C6 alkoxy group, a C2-C6 alkenyl group, a linear, branched or cyclic C1-C6 fluoroalkyl group, a $N(R^4)_2$ group (wherein $R^4$ represents a hydrogen atom, a phenyl group, a benzyl group, or a linear, branched or cyclic C1-C6 alkyl group), a $NHCOR^5$ group (wherein $R^5$ represents a linear, branched or cyclic C1-C6 alkyl group), an optionally substituted phenyl group, or an optionally substituted benzyl group;
n1 and n3 each independently represent any integer of 1 to 5;
two groups represented by $R^3$ adjacent to each other on a benzene ring optionally bond to each other to form an optionally substituted 6-membered ring; and n2 represents any integer of 1 to 4).

(4) A compound represented by the following formula (I):

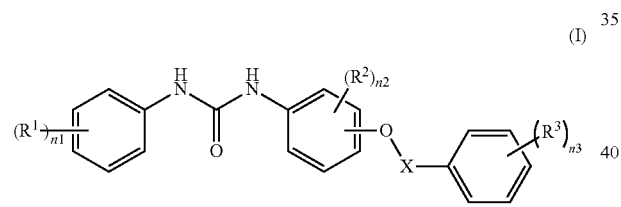

(wherein X represents $CH_2$, $C=O$, or $SO_2$;
$R^1$ to $R^3$ each independently represent a hydrogen atom, a halogen atom, a nitro group, a cyano group, a linear, branched or cyclic C1-C6 alkylcarbonyl group, a linear, branched or cyclic C1-C6 alkyl group, a linear, branched or cyclic C1-C6 alkoxy group, a C2-C6 alkenyl group, a linear, branched or cyclic C1-C6 fluoroalkyl group, a $N(R^4)_2$ group (wherein $R^4$ represents a hydrogen atom, a phenyl group, a benzyl group, or a linear, branched or cyclic C1-C6 alkyl group), a $NHCOR^5$ group (wherein $R^5$ represents a linear, branched or cyclic C1-C6 alkyl group), an optionally substituted phenyl group, or an optionally substituted benzyl group;
n1 and n3 each independently represent any integer of 1 to 5;
two groups represented by $R^3$ adjacent to each other on a benzene ring optionally bond to each other to form an optionally substituted 6-membered ring; and n2 represents any integer of 1 to 4).

Effect of the Invention

According to the present invention, a recording material or a recording sheet good in color developing performance and storage property may be obtained. In particular, a recording material having improved color-developing sensitivity and excellent in a background heat resistance and an image water resistance may be obtained.

MODE OF CARRYING OUT THE INVENTION (Compound represented by formula (I))

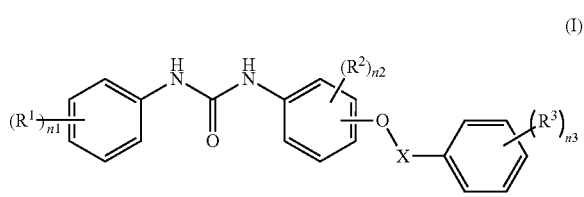

A compound represented by a formula (I) is described below.
In the formula (I), X represents $CH_2$, $C=O$, or $SO_2$.
The compound represented by the formula (I) is a compound represented by any of the following formulas (II), (III) and (IV):

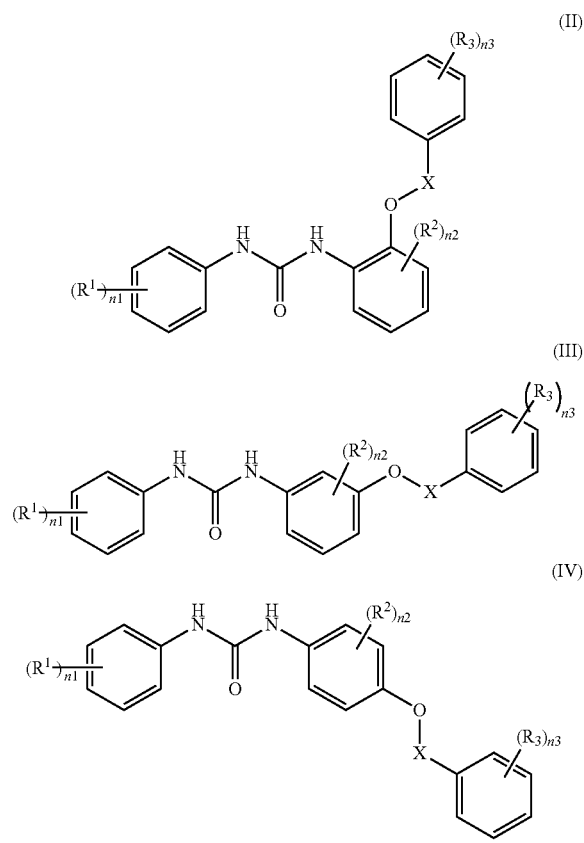

Among them, the compound represented by the formula (III) is preferred in terms of performances such as a color-developing property.
In particular, when X=CO, the compound represented by the formula (III) or the formula (IV) is preferred, and the compound represented by the formula (III) is more preferred. Besides, when $X=SO_2$, the compound represented by the formula (III) is preferred.

In the formula (I), as $R^1$ to $R^3$, the following may be exemplified:

a hydrogen atom;

a halogen atom such as a fluorine atom, a chlorine atom, a bromine atom or an iodine atom;

a nitro group;

a cyano group;

a straight, branched or cyclic C1-C6 alkyl group such as methyl, ethyl, propyl, isopropyl, n-butyl, isobutyl, sec-butyl, t-butyl, n-pentyl, isopentyl, neopentyl, n-hexyl, isohexyl, cyclopropyl, cyclobutyl, 2-methylcyclopropyl, cyclopropylmethyl, cyclopentyl, or cyclohexyl;

a straight, branched or cyclic C1-C6 alkoxy group such as methoxy, ethoxy, propoxy, isopropoxy, n-butoxy, isobutoxy, sec-butoxy, t-butoxy, n-pentyloxy, isopentyloxy, n-hexyloxy, cyclopropoxy, cyclobutoxy, 2-methylcyclopropoxy, cyclopropylmethoxy, cyclopentyloxy, or cyclohexyloxy; a straight, branched or cyclic C1-C6 alkylcarbonyl group such as methylcarbonyl, ethylcarbonyl, propylcarbonyl, isopropylcarbonyl, n-butylcarbonyl, isobutylcarbonyl, sec-butylcarbonyl, t-butylcarbonyl, n-pentylcarbonyl, isopentylcarbonyl, neopentylcarbonyl, n-hexylcarbonyl, isohexylcarbonyl, cyclopropylcarbonyl, cyclobutylcarbonyl, 2-methylcyclopropylcarbonyl, cyclopropylmethylcarbonyl, cyclopentylcarbonyl, or cyclohexylcarbonyl;

a C2-C6 alkenyl group such as a vinyl group, an allyl group, an isopropenyl group, a 1-propenyl group, a 2-propenyl group, a 1-butenyl group, a 2-butenyl group, a 3-butenyl group, a 1,3-butanedienyl group, or a 2-methyl-2-propenyl group;

a straight, branched or cyclic C1-C6 fluoroalkyl group such as a trifluoromethyl group, a perfluoroethyl group, a perfluoropropyl group, a perfluorobutyl group, a perfluorohexyl group, or a perfluorocyclohexyl group;

a $N(R^4)_2$ group (wherein $R^4$ represents a hydrogen atom, a phenyl group, a benzyl group, or a linear, branched or cyclic C1-C6 alkyl group);

$NHCOR^5$ (wherein $R^5$ represents a linear, branched or cyclic C1-C6 alkyl group);

an optionally substituted phenyl group;

an optionally substituted benzyl group, and the like.

Besides, when at least two $R^3$s are present in adjacent positions on a benzene ring, the two $R^3$s adjacent to each other optionally bond to each other to form, together with carbon atoms of the benzene ring directly bonded thereto, an optionally substituted 6-membered ring. Specifically, a compound in which a naphthalene ring (bonded to X at either the 1- or the 2-position) is formed together with the benzene ring by forming an optionally substituted 1,3-dibuten-1,4-yl group through mutual bond of the two $R^3$s adjacent to each other; a compound in which a 1,2-dihydronaphthalene ring (bonded to X in any of the 5-, the 6-, the 7- and the 8-positions) is formed together with the benzene ring by forming an optionally substituted 1-buten-1,4-yl group through mutual bond of the two $R^3$s adjacent to each other; a compound in which a 1,4-dihydronaphthalene ring (bonded to X in either the 5- or the 6-position) together with the benzene ring by forming an optionally substituted 2-buten-1,4-yl group through mutual bond of the two $R^3$s adjacent to each other; and a compound in which a tetralin ring (bonded to X in either the 1- or the 2-position) together with the benzene ring by forming an optionally substituted butan-1,4-yl group through mutual bond of the two $R^3$s adjacent to each other may be exemplified.

Preferably, $R^1$ represents a hydrogen atom, a linear C1-C6 alkyl group, a linear C1-C6 alkoxy group, a chlorine atom or a nitro group, $R^2$ represents a hydrogen atom, and $R^3$ represents a hydrogen atom or a linear C1-C6 alkyl group.

As the linear, branched or cyclic C1-C6 alkyl group of $R^4$ or $R^5$, the same as those exemplified as the linear, branched or cyclic C1-C6 alkyl group of $R^1$ may be exemplified.

Here, examples of the substituent in "optionally substituted" group include:

a halogen atom such as a fluorine atom, a chlorine atom, a bromine atom, or an iodine atom;

a C1-C6 alkyl group such as a methyl group, an ethyl group, a n-propyl group, an isopropyl group, a n-butyl group, a sec-butyl group, a t-butyl group, a n-pentyl group, an isopentyl group, a neopentyl group, a t-pentyl group, a n-hexyl group, an isohexyl group, a 1-methyl pentyl group, or a 2-methyl pentyl group; and a C1-C6 alkoxy group such as a methoxy group, an ethoxy group, a n-propoxy group, an isopropoxy group, a n-butoxy group, a sec-butoxy group, or a t-butoxy group.

n1 and n3 each independently represent any integer of 1 to 5, and n2 represents any integer of 1 to 4.

As representative compounds represented by the formula (I), 1-(3-benzyloxyphenyl)-3-(3-chlorophenyl)urea, 3-(3-phenylureido)phenyl benzoate, and 3-(3-(3-chlorophenyl)ureido)phenyl-4-methylbenzenesulfonate may be exemplified.

(Method for Producing Compound Represented by Formula (I))

The compound represented by the formula (I) may be produced by any method as long as the compound can be produced, and may be produced by any of various known methods such as production methods 1 to 4 described below.

(Production Method 1)

The compound represented by the formula (I) may be produced by reacting an aniline derivative represented by a general formula (V):

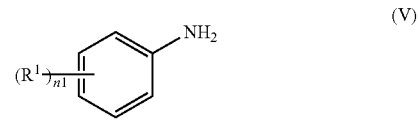

(wherein $R^1$ and n1 represent the same as those in the formula (I)) with an isocyanate derivative represented by a general formula (VI):

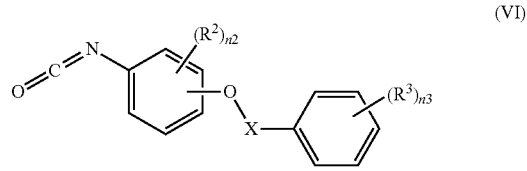

(wherein $R^2$, $R^3$, n2, n3 and X represent the same as those in the formula (I)).

(Production Method 2)

Alternatively, when X is $CH_2$, the compound represented by the formula (I) may be also produced through steps (1) and (2) described below.

(1) A step of reacting an aminophenol derivative represented by a general formula (VII):

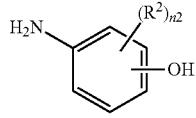
(VII)

(wherein $R^2$ and n2 represent the same as those in the formula (I)) with an isocyanate derivative represented by a general formula (VIII):

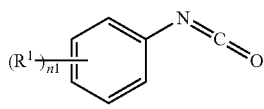
(VIII)

(wherein $R^1$ and n1 represent the same as those in the formula (I)) to obtain a phenol derivative represented by a general formula (IX):

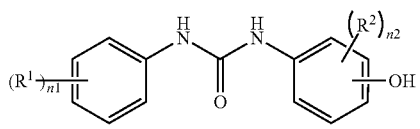
(IX)

(wherein $R^1$, $R^2$, n1 and n2 represent the same as those in the formula (VII) and the formula (VIII)).

(2) A step of reacting the phenol derivative represented by the formula (IX) with a benzyl chloride derivative represented by a general formula (X):

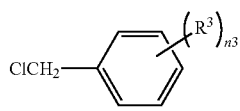
(X)

(wherein $R^3$ and n3 represent the same as those in the formula (I)) to obtain the compound represented by the formula (I).

(Production Method 3)
Alternatively, when X is C=O, the compound represented by the formula (I) may be produced through a step (2') described below following the step (1) the same as that of the production method 2.

(2') A step of reacting the phenol derivative represented by the formula (IX) with a benzoyl chloride derivative represented by a general formula (XI):

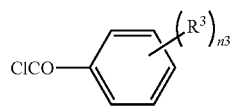
(XI)

(wherein $R^3$ and n3 represent the same as those in the formula (I)) or with a benzoic anhydride derivative represented by a general formula (XII):

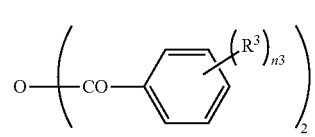
(XII)

(wherein $R^3$ and n3 represent the same as those in the formula (I)) to obtain the compound represented by the formula (I).

(Production Method 4)
Alternatively, when X is $SO_2$, the compound represented by the formula (I) may be also produced through a step (2") described below following the step (1) the same as that of the production method 2.

(2") A step of reacting the phenol derivative represented by the formula (IX) with a benzenesulfonyl chloride derivative represented by a general formula (XIII):

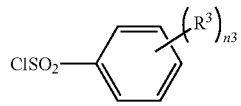
(XIII)

(wherein $R^3$ and n3 represent the same as those in the formula (I)), or with a benzenesulfonic acid derivative represented by a general formula (XIV) or a salt thereof:

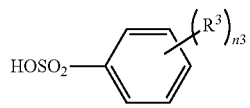
(XIV)

(wherein $R^3$ and n3 represent the same as those in the formula (I)) to obtain the compound represented by the formula (I).

The compounds of the present invention can be identified in their structure by measuring $^1$H-NMR, $^{13}$C-NMR, IR, MS or the like by using a known measuring apparatus. Besides, the purity can be measured by using a measuring apparatus for liquid chromatography (HPLC), thermal analysis (DSC) or the like.

Furthermore, examples of a compound that can be thus synthesized are shown in Table 1.

TABLE 1

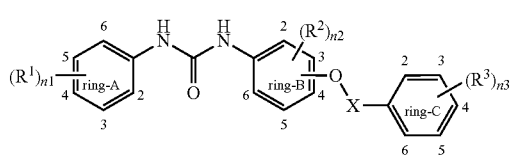

(Numbers shown around ring-A to ring-C in the formula above indicate positions on the rings. Similarly, numbers shown in the columns of ring-A to ring-C in the following tables indicate the positions on the rings.)

TABLE 1

| Compound No. | ring-A ($R^1$)n1 | | | | | ring-B ($R^2$)n2 and O-X-ring-C | | | | | Ring-C ($R^3$)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 1 | H | H | H | H | H | OCH$_2$-ringC | H | H | H | H | H | H | H | H | H | 172-173 |
| 2 | Cl | H | H | H | H | OCH$_2$-ringC | H | H | H | H | H | H | H | H | H | |
| 3 | H | Cl | H | H | H | OCH$_2$-ringC | H | H | H | H | H | H | H | H | H | |
| 4 | H | H | Cl | H | H | OCH$_2$-ringC | H | H | H | H | H | H | H | H | H | 200-201 |
| 5 | Me | H | H | H | H | OCH$_2$-ringC | H | H | H | H | H | H | H | H | H | |
| 6 | H | Me | H | H | H | OCH$_2$-ringC | H | H | H | H | H | H | H | H | H | |
| 7 | H | H | Me | H | H | OCH$_2$-ringC | H | H | H | H | H | H | H | H | H | |
| 8 | OMe | H | H | H | H | OCH$_2$-ringC | H | H | H | H | H | H | H | H | H | |
| 9 | H | OMe | H | H | H | OCH$_2$-ringC | H | H | H | H | H | H | H | H | H | |
| 10 | H | H | OMe | H | H | OCH$_2$-ringC | H | H | H | H | H | H | H | H | H | |
| 11 | H | H | NHAc | H | H | OCH$_2$-ringC | H | H | H | H | H | H | H | H | H | |
| 12 | H | H | Ac | H | H | OCH$_2$-ringC | H | H | H | H | H | H | H | H | H | |
| 13 | NO$_2$ | H | H | H | H | OCH$_2$-ringC | H | H | H | H | H | H | H | H | H | |
| 14 | H | NO$_2$ | H | H | H | OCH$_2$-ringC | H | H | H | H | H | H | H | H | H | |
| 15 | H | H | NO$_2$ | H | H | OCH$_2$-ringC | H | H | H | H | H | H | H | H | H | |
| 16 | CN | H | H | H | H | OCH$_2$-ringC | H | H | H | H | H | H | H | H | H | |
| 17 | H | CN | H | H | H | OCH$_2$-ringC | H | H | H | H | H | H | H | H | H | |
| 18 | H | H | CN | H | H | OCH$_2$-ringC | H | H | H | H | H | H | H | H | H | |
| 19 | H | H | H | H | H | OCH$_2$-ringC | H | H | H | H | H | H | Me | H | H | |
| 20 | Cl | H | H | H | H | OCH$_2$-ringC | H | H | H | H | H | H | Me | H | H | |
| 21 | H | Cl | H | H | H | OCH$_2$-ringC | H | H | H | H | H | H | Me | H | H | |
| 22 | H | H | Cl | H | H | OCH$_2$-ringC | H | H | H | H | H | H | Me | H | H | |
| 23 | Me | H | H | H | H | OCH$_2$-ringC | H | H | H | H | H | H | Me | H | H | |
| 24 | H | Me | H | H | H | OCH$_2$-ringC | H | H | H | H | H | H | Me | H | H | |
| 25 | H | H | Me | H | H | OCH$_2$-ringC | H | H | H | H | H | H | Me | H | H | |
| 26 | OMe | H | H | H | H | OCH$_2$-ringC | H | H | H | H | H | H | Me | H | H | |
| 27 | H | OMe | H | H | H | OCH$_2$-ringC | H | H | H | H | H | H | Me | H | H | |
| 28 | H | H | OMe | H | H | OCH$_2$-ringC | H | H | H | H | H | H | Me | H | H | |
| 29 | NO$_2$ | H | H | H | H | OCH$_2$-ringC | H | H | H | H | H | H | Me | H | H | |
| 30 | H | NO$_2$ | H | H | H | OCH$_2$-ringC | H | H | H | H | H | H | Me | H | H | |
| 31 | H | H | NO$_2$ | H | H | OCH$_2$-ringC | H | H | H | H | H | H | Me | H | H | |
| 32 | CN | H | H | H | H | OCH$_2$-ringC | H | H | H | H | H | H | Me | H | H | |
| 33 | H | CN | H | H | H | OCH$_2$-ringC | H | H | H | H | H | H | Me | H | H | |
| 34 | H | H | CN | H | H | OCH$_2$-ringC | H | H | H | H | H | H | Me | H | H | |
| 35 | H | H | H | H | H | OCH$_2$-ringC | H | H | H | H | H | H | OMe | H | H | |
| 36 | Cl | H | H | H | H | OCH$_2$-ringC | H | H | H | H | H | H | OMe | H | H | |
| 37 | H | Cl | H | H | H | OCH$_2$-ringC | H | H | H | H | H | H | OMe | H | H | |

TABLE 1-continued

| Compound No. | ring-A (R¹)n1 | | | | | ring-B (R²)n2 and O-X-ring-C | | | | | Ring-C (R³)n3 | | | | | Melting point (° C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 38 | H | H | Cl | H | H | OCH₂-ringC | H | H | H | H | H | H | OMe | H | H | |
| 39 | Me | H | H | H | H | OCH₂-ringC | H | H | H | H | H | H | OMe | H | H | |
| 40 | H | Me | H | H | H | OCH₂-ringC | H | H | H | H | H | H | OMe | H | H | |
| 41 | H | H | Me | H | H | OCH₂-ringC | H | H | H | H | H | H | OMe | H | H | |
| 42 | OMe | H | H | H | H | OCH₂-ringC | H | H | H | H | H | H | OMe | H | H | |
| 43 | H | OMe | H | H | H | OCH₂-ringC | H | H | H | H | H | H | OMe | H | H | |
| 44 | H | H | OMe | H | H | OCH₂-ringC | H | H | H | H | H | H | OMe | H | H | |
| 45 | NO₂ | H | H | H | H | OCH₂-ringC | H | H | H | H | H | H | OMe | H | H | |
| 46 | H | NO₂ | H | H | H | OCH₂-ringC | H | H | H | H | H | H | OMe | H | H | |
| 47 | H | H | NO₂ | H | H | OCH₂-ringC | H | H | H | H | H | H | OMe | H | H | |
| 48 | CN | H | H | H | H | OCH₂-ringC | H | H | H | H | H | H | OMe | H | H | |
| 49 | H | CN | H | H | H | OCH₂-ringC | H | H | H | H | H | H | OMe | H | H | |
| 50 | H | H | CN | H | H | OCH₂-ringC | H | H | H | H | H | H | OMe | H | H | |
| 51 | H | H | H | H | H | OCH₂-ringC | H | H | H | H | H | H | Cl | H | H | |
| 52 | Cl | H | H | H | H | OCH₂-ringC | H | H | H | H | H | H | Cl | H | H | |
| 53 | H | Cl | H | H | H | OCH₂-ringC | H | H | H | H | H | H | Cl | H | H | |
| 54 | H | H | Cl | H | H | OCH₂-ringC | H | H | H | H | H | H | Cl | H | H | |
| 55 | Me | H | H | H | H | OCH₂-ringC | H | H | H | H | H | H | Cl | H | H | |
| 56 | H | Me | H | H | H | OCH₂-ringC | H | H | H | H | H | H | Cl | H | H | |
| 57 | H | H | Me | H | H | OCH₂-ringC | H | H | H | H | H | H | Cl | H | H | |
| 58 | OMe | H | H | H | H | OCH₂-ringC | H | H | H | H | H | H | Cl | H | H | |
| 59 | H | OMe | H | H | H | OCH₂-ringC | H | H | H | H | H | H | Cl | H | H | |
| 60 | H | H | OMe | H | H | OCH₂-ringC | H | H | H | H | H | H | Cl | H | H | |
| 61 | NO₂ | H | H | H | H | OCH₂-ringC | H | H | H | H | H | H | Cl | H | H | |
| 62 | H | NO₂ | H | H | H | OCH₂-ringC | H | H | H | H | H | H | Cl | H | H | |
| 63 | H | H | NO₂ | H | H | OCH₂-ringC | H | H | H | H | H | H | Cl | H | H | |
| 64 | CN | H | H | H | H | OCH₂-ringC | H | H | H | H | H | H | Cl | H | H | |
| 65 | H | CN | H | H | H | OCH₂-ringC | H | H | H | H | H | H | Cl | H | H | |
| 66 | H | H | CN | H | H | OCH₂-ringC | H | H | H | H | H | H | Cl | H | H | |
| 67 | H | H | H | H | H | OCO-ringC | H | H | H | H | H | H | H | H | H | 171-174 |
| 68 | Cl | H | H | H | H | OCO-ringC | H | H | H | H | H | H | H | H | H | |
| 69 | H | Cl | H | H | H | OCO-ringC | H | H | H | H | H | H | H | H | H | |
| 70 | H | H | Cl | H | H | OCO-ringC | H | H | H | H | H | H | H | H | H | 206-207 |
| 71 | Me | H | H | H | H | OCO-ringC | H | H | H | H | H | H | H | H | H | |
| 72 | H | Me | H | H | H | OCO-ringC | H | H | H | H | H | H | H | H | H | |
| 73 | H | H | Me | H | H | OCO-ringC | H | H | H | H | H | H | H | H | H | |
| 74 | OMe | H | H | H | H | OCO-ringC | H | H | H | H | H | H | H | H | H | |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 75 | H | OMe | H | H | H | OCO-ringC | H | H | H | H | H | H | H | H | H | |
| 76 | H | H | OMe | H | H | OCO-ringC | H | H | H | H | H | H | H | H | H | |
| 77 | H | H | NHAc | H | H | OCO-ringC | H | H | H | H | H | H | H | H | H | |
| 78 | H | H | Ac | H | H | OCO-ringC | H | H | H | H | H | H | H | H | H | |
| 79 | NO₂ | H | H | H | H | OCO-ringC | H | H | H | H | H | H | H | H | H | |
| 80 | H | NO₂ | H | H | H | OCO-ringC | H | H | H | H | H | H | H | H | H | |
| 81 | H | H | NO₂ | H | H | OCO-ringC | H | H | H | H | H | H | H | H | H | |
| 82 | CN | H | H | H | H | OCO-ringC | H | H | H | H | H | H | H | H | H | |
| 83 | H | CN | H | H | H | OCO-ringC | H | H | H | H | H | H | H | H | H | |
| 84 | H | H | CN | H | H | OCO-ringC | H | H | H | H | H | H | H | H | H | |
| 85 | H | H | H | H | H | OCO-ringC | H | H | H | H | H | H | Me | H | H | |
| 86 | Cl | H | H | H | H | OCO-ringC | H | H | H | H | H | H | Me | H | H | |
| 87 | H | Cl | H | H | H | OCO-ringC | H | H | H | H | H | H | Me | H | H | |
| 88 | H | H | Cl | H | H | OCO-ringC | H | H | H | H | H | H | Me | H | H | |
| 89 | Me | H | H | H | H | OCO-ringC | H | H | H | H | H | H | Me | H | H | |
| 90 | H | Me | H | H | H | OCO-ringC | H | H | H | H | H | H | Me | H | H | |
| 91 | H | H | Me | H | H | OCO-ringC | H | H | H | H | H | H | Me | H | H | |
| 92 | OMe | H | H | H | H | OCO-ringC | H | H | H | H | H | H | Me | H | H | |
| 93 | H | OMe | H | H | H | OCO-ringC | H | H | H | H | H | H | Me | H | H | |
| 94 | H | H | OMe | H | H | OCO-ringC | H | H | H | H | H | H | Me | H | H | |
| 95 | NO₂ | H | H | H | H | OCO-ringC | H | H | H | H | H | H | Me | H | H | |
| 96 | H | NO₂ | H | H | H | OCO-ringC | H | H | H | H | H | H | Me | H | H | |
| 97 | H | H | NO₂ | H | H | OCO-ringC | H | H | H | H | H | H | Me | H | H | |
| 98 | CN | H | H | H | H | OCO-ringC | H | H | H | H | H | H | Me | H | H | |
| 99 | H | CN | H | H | H | OCO-ringC | H | H | H | H | H | H | Me | H | H | |
| 100 | H | H | CN | H | H | OCO-ringC | H | H | H | H | H | H | Me | H | H | |
| 101 | H | H | H | H | H | OCO-ringC | H | H | H | H | H | H | OMe | H | H | |
| 102 | Cl | H | H | H | H | OCO-ringC | H | H | H | H | H | H | OMe | H | H | |
| 103 | H | Cl | H | H | H | OCO-ringC | H | H | H | H | H | H | OMe | H | H | |
| 104 | H | H | Cl | H | H | OCO-ringC | H | H | H | H | H | H | OMe | H | H | |
| 105 | Me | H | H | H | H | OCO-ringC | H | H | H | H | H | H | OMe | H | H | |
| 106 | H | Me | H | H | H | OCO-ringC | H | H | H | H | H | H | OMe | H | H | |
| 107 | H | H | Me | H | H | OCO-ringC | H | H | H | H | H | H | OMe | H | H | |
| 108 | OMe | H | H | H | H | OCO-ringC | H | H | H | H | H | H | OMe | H | H | |
| 109 | H | OMe | H | H | H | OCO-ringC | H | H | H | H | H | H | OMe | H | H | |
| 110 | H | H | OMe | H | H | OCO-ringC | H | H | H | H | H | H | OMe | H | H | |
| 111 | NO₂ | H | H | H | H | OCO-ringC | H | H | H | H | H | H | OMe | H | H | |

TABLE 1-continued

| Compound No. | ring-A (R¹)n1 | | | | | ring-B (R²)n2 and O-X-ring-C | | | | | Ring-C (R³)n3 | | | | | Melting point (° C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 112 | H | NO₂ | H | H | H | OCO-ringC | H | H | H | H | H | H | OMe | H | H | |
| 113 | H | H | NO₂ | H | H | OCO-ringC | H | H | H | H | H | H | OMe | H | H | |
| 114 | CN | H | H | H | H | OCO-ringC | H | H | H | H | H | H | OMe | H | H | |
| 115 | H | CN | H | H | H | OCO-ringC | H | H | H | H | H | H | OMe | H | H | |
| 116 | H | H | CN | H | H | OCO-ringC | H | H | H | H | H | H | OMe | H | H | |
| 117 | H | H | H | H | H | OCO-ringC | H | H | H | H | H | H | Cl | H | H | |
| 118 | Cl | H | H | H | H | OCO-ringC | H | H | H | H | H | H | Cl | H | H | |
| 119 | H | Cl | H | H | H | OCO-ringC | H | H | H | H | H | H | Cl | H | H | |
| 120 | H | H | Cl | H | H | OCO-ringC | H | H | H | H | H | H | Cl | H | H | |
| 121 | Me | H | H | H | H | OCO-ringC | H | H | H | H | H | H | Cl | H | H | |
| 122 | H | Me | H | H | H | OCO-ringC | H | H | H | H | H | H | Cl | H | H | |
| 123 | H | H | Me | H | H | OCO-ringC | H | H | H | H | H | H | Cl | H | H | |
| 124 | OMe | H | H | H | H | OCO-ringC | H | H | H | H | H | H | Cl | H | H | |
| 125 | H | OMe | H | H | H | OCO-ringC | H | H | H | H | H | H | Cl | H | H | |
| 126 | H | H | OMe | H | H | OCO-ringC | H | H | H | H | H | H | Cl | H | H | |
| 127 | NO₂ | H | H | H | H | OCO-ringC | H | H | H | H | H | H | Cl | H | H | |
| 128 | H | NO₂ | H | H | H | OCO-ringC | H | H | H | H | H | H | Cl | H | H | |
| 129 | H | H | NO₂ | H | H | OCO-ringC | H | H | H | H | H | H | Cl | H | H | |
| 130 | CN | H | H | H | H | OCO-ringC | H | H | H | H | H | H | Cl | H | H | |
| 131 | H | CN | H | H | H | OCO-ringC | H | H | H | H | H | H | Cl | H | H | |
| 132 | H | H | CN | H | H | OCO-ringC | H | H | H | H | H | H | Cl | H | H | |
| 133 | H | H | H | H | H | OSO₂-ringC | H | H | H | H | H | H | H | H | H | |
| 134 | Cl | H | H | H | H | OSO₂-ringC | H | H | H | H | H | H | H | H | H | |
| 135 | H | Cl | H | H | H | OSO₂-ringC | H | H | H | H | H | H | H | H | H | |
| 136 | H | H | Cl | H | H | OSO₂-ringC | H | H | H | H | H | H | H | H | H | |
| 137 | Me | H | H | H | H | OSO₂-ringC | H | H | H | H | H | H | H | H | H | |
| 138 | H | Me | H | H | H | OSO₂-ringC | H | H | H | H | H | H | H | H | H | |
| 139 | H | H | Me | H | H | OSO₂-ringC | H | H | H | H | H | H | H | H | H | |
| 140 | OMe | H | H | H | H | OSO₂-ringC | H | H | H | H | H | H | H | H | H | |
| 141 | H | OMe | H | H | H | OSO₂-ringC | H | H | H | H | H | H | H | H | H | |
| 142 | H | H | OMe | H | H | OSO₂-ringC | H | H | H | H | H | H | H | H | H | |
| 143 | NO₂ | H | H | H | H | OSO₂-ringC | H | H | H | H | H | H | H | H | H | |
| 144 | H | NO₂ | H | H | H | OSO₂-ringC | H | H | H | H | H | H | H | H | H | |
| 145 | H | H | NO₂ | H | H | OSO₂-ringC | H | H | H | H | H | H | H | H | H | |
| 146 | CN | H | H | H | H | OSO₂-ringC | H | H | H | H | H | H | H | H | H | |
| 147 | H | CN | H | H | H | OSO₂-ringC | H | H | H | H | H | H | H | H | H | |
| 148 | H | H | CN | H | H | OSO₂-ringC | H | H | H | H | H | H | H | H | H | |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 149 | H | H | H | H | H | OSO₂-ringC | H | H | H | H | H | H | Me | H | H | 173-174 |
| 150 | Cl | H | H | H | H | OSO₂-ringC | H | H | H | H | H | H | Me | H | H | |
| 151 | H | Cl | H | H | H | OSO₂-ringC | H | H | H | H | H | H | Me | H | H | |
| 152 | H | H | Cl | H | H | OSO₂-ringC | H | H | H | H | H | H | Me | H | H | 144-147 |
| 153 | Me | H | H | H | H | OSO₂-ringC | H | H | H | H | H | H | Me | H | H | |
| 154 | H | Me | H | H | H | OSO₂-ringC | H | H | H | H | H | H | Me | H | H | |
| 155 | H | H | Me | H | H | OSO₂-ringC | H | H | H | H | H | H | Me | H | H | |
| 156 | OMe | H | H | H | H | OSO₂-ringC | H | H | H | H | H | H | Me | H | H | |
| 157 | H | OMe | H | H | H | OSO₂-ringC | H | H | H | H | H | H | Me | H | H | |
| 158 | H | H | OMe | H | H | OSO₂-ringC | H | H | H | H | H | H | Me | H | H | |
| 159 | H | H | NHAc | H | H | OSO₂-ringC | H | H | H | H | H | H | Me | H | H | |
| 160 | H | H | Ac | H | H | OSO₂-ringC | H | H | H | H | H | H | Me | H | H | |
| 161 | NO₂ | H | H | H | H | OSO₂-ringC | H | H | H | H | H | H | Me | H | H | |
| 162 | H | NO₂ | H | H | H | OSO₂-ringC | H | H | H | H | H | H | Me | H | H | |
| 163 | H | H | NO₂ | H | H | OSO₂-ringC | H | H | H | H | H | H | Me | H | H | |
| 164 | CN | H | H | H | H | OSO₂-ringC | H | H | H | H | H | H | Me | H | H | |
| 165 | H | CN | H | H | H | OSO₂-ringC | H | H | H | H | H | H | Me | H | H | |
| 166 | H | H | CN | H | H | OSO₂-ringC | H | H | H | H | H | H | Me | H | H | |
| 167 | H | H | H | H | H | OSO₂-ringC | H | H | H | H | H | H | OMe | H | H | |
| 168 | Cl | H | H | H | H | OSO₂-ringC | H | H | H | H | H | H | OMe | H | H | |
| 169 | H | Cl | H | H | H | OSO₂-ringC | H | H | H | H | H | H | OMe | H | H | |
| 170 | H | H | Cl | H | H | OSO₂-ringC | H | H | H | H | H | H | OMe | H | H | |
| 171 | Me | H | H | H | H | OSO₂-ringC | H | H | H | H | H | H | OMe | H | H | |
| 172 | H | Me | H | H | H | OSO₂-ringC | H | H | H | H | H | H | OMe | H | H | |
| 173 | H | H | Me | H | H | OSO₂-ringC | H | H | H | H | H | H | OMe | H | H | |
| 174 | OMe | H | H | H | H | OSO₂-ringC | H | H | H | H | H | H | OMe | H | H | |
| 175 | H | OMe | H | H | H | OSO₂-ringC | H | H | H | H | H | H | OMe | H | H | |
| 176 | H | H | OMe | H | H | OSO₂-ringC | H | H | H | H | H | H | OMe | H | H | |
| 177 | H | H | NHAc | H | H | OSO₂-ringC | H | H | H | H | H | H | OMe | H | H | |
| 178 | H | H | Ac | H | H | OSO₂-ringC | H | H | H | H | H | H | OMe | H | H | |
| 179 | NO₂ | H | H | H | H | OSO₂-ringC | H | H | H | H | H | H | OMe | H | H | |
| 180 | H | NO₂ | H | H | H | OSO₂-ringC | H | H | H | H | H | H | OMe | H | H | |
| 181 | H | H | NO₂ | H | H | OSO₂-ringC | H | H | H | H | H | H | OMe | H | H | |
| 182 | CN | H | H | H | H | OSO₂-ringC | H | H | H | H | H | H | OMe | H | H | |
| 183 | H | CN | H | H | H | OSO₂-ringC | H | H | H | H | H | H | OMe | H | H | |
| 184 | H | H | CN | H | H | OSO₂-ringC | H | H | H | H | H | H | OMe | H | H | |
| 185 | H | H | H | H | H | OSO₂-ringC | H | H | H | H | H | H | Cl | H | H | |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 186 | Cl | H | H | H | H | OSO₂-ringC | H | H | H | H | H | H | Cl | H | H | |
| 187 | H | Cl | H | H | H | OSO₂-ringC | H | H | H | H | H | H | Cl | H | H | |
| 188 | H | H | Cl | H | H | OSO₂-ringC | H | H | H | H | H | H | Cl | H | H | |
| 189 | Me | H | H | H | H | OSO₂-ringC | H | H | H | H | H | H | Cl | H | H | |
| 190 | H | Me | H | H | H | OSO₂-ringC | H | H | H | H | H | H | Cl | H | H | |
| 191 | H | H | Me | H | H | OSO₂-ringC | H | H | H | H | H | H | Cl | H | H | |
| 192 | OMe | H | H | H | H | OSO₂-ringC | H | H | H | H | H | H | Cl | H | H | |
| 193 | H | OMe | H | H | H | OSO₂-ringC | H | H | H | H | H | H | Cl | H | H | |
| 194 | H | H | OMe | H | H | OSO₂-ringC | H | H | H | H | H | H | Cl | H | H | |
| 195 | H | H | NHAc | H | H | OSO₂-ringC | H | H | H | H | H | H | Cl | H | H | |
| 196 | H | H | Ac | H | H | OSO₂-ringC | H | H | H | H | H | H | Cl | H | H | |
| 197 | NO₂ | H | H | H | H | OSO₂-ringC | H | H | H | H | H | H | Cl | H | H | |
| 198 | H | NO₂ | H | H | H | OSO₂-ringC | H | H | H | H | H | H | Cl | H | H | |
| 199 | H | H | NO₂ | H | H | OSO₂-ringC | H | H | H | H | H | H | Cl | H | H | |
| 200 | CN | H | H | H | H | OSO₂-ringC | H | H | H | H | H | H | Cl | H | H | |
| 201 | H | CN | H | H | H | OSO₂-ringC | H | H | H | H | H | H | Cl | H | H | |
| 202 | H | H | CN | H | H | OSO₂-ringC | H | H | H | H | H | H | Cl | H | H | |
| 203 | H | H | H | H | H | H | OCH₂-ringC | H | H | H | H | H | H | H | H | 179-182 |
| 204 | Cl | H | H | H | H | H | OCH₂-ringC | H | H | H | H | H | H | H | H | 163-164 |
| 205 | H | Cl | H | H | H | H | OCH₂-ringC | H | H | H | H | H | H | H | H | 174-175 |
| 206 | H | H | Cl | H | H | H | OCH₂-ringC | H | H | H | H | H | H | H | H | 197-198 |
| 207 | Me | H | H | H | H | H | OCH₂-ringC | H | H | H | H | H | H | H | H | |
| 208 | H | Me | H | H | H | H | OCH₂-ringC | H | H | H | H | H | H | H | H | |
| 209 | H | H | Me | H | H | H | OCH₂-ringC | H | H | H | H | H | H | H | H | |
| 210 | OMe | H | H | H | H | H | OCH₂-ringC | H | H | H | H | H | H | H | H | |
| 211 | H | OMe | H | H | H | H | OCH₂-ringC | H | H | H | H | H | H | H | H | |
| 212 | H | H | OMe | H | H | H | OCH₂-ringC | H | H | H | H | H | H | H | H | |
| 213 | H | H | NHAc | H | H | H | OCH₂-ringC | H | H | H | H | H | H | H | H | |
| 214 | H | H | Ac | H | H | H | OCH₂-ringC | H | H | H | H | H | H | H | H | |
| 215 | NO₂ | H | H | H | H | H | OCH₂-ringC | H | H | H | H | H | H | H | H | |
| 216 | H | NO₂ | H | H | H | H | OCH₂-ringC | H | H | H | H | H | H | H | H | |
| 217 | H | H | NO₂ | H | H | H | OCH₂-ringC | H | H | H | H | H | H | H | H | |
| 218 | CN | H | H | H | H | H | OCH₂-ringC | H | H | H | H | H | H | H | H | |
| 219 | H | CN | H | H | H | H | OCH₂-ringC | H | H | H | H | H | H | H | H | |
| 220 | H | H | CN | H | H | H | OCH₂-ringC | H | H | H | H | H | H | H | H | |
| 221 | H | H | H | H | H | H | OCO-ringC | H | H | H | H | H | H | H | H | 174-179 |
| 222 | Cl | H | H | H | H | H | OCO-ringC | H | H | H | H | H | H | H | H | 178-179 |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 223 | H | Cl | H | H | H | H | OCO-ringC | H | H | H | H | H | H | H | H | 200-201 |
| 224 | H | H | Cl | H | H | H | OCO-ringC | H | H | H | H | H | H | H | H | 209-210 |
| 225 | Me | H | H | H | H | H | OCO-ringC | H | H | H | H | H | H | H | H | |
| 226 | H | Me | H | H | H | H | OCO-ringC | H | H | H | H | H | H | H | H | |
| 227 | H | H | Me | H | H | H | OCO-ringC | H | H | H | H | H | H | H | H | |
| 228 | OMe | H | H | H | H | H | OCO-ringC | H | H | H | H | H | H | H | H | |
| 229 | H | OMe | H | H | H | H | OCO-ringC | H | H | H | H | H | H | H | H | |
| 230 | H | H | OMe | H | H | H | OCO-ringC | H | H | H | H | H | H | H | H | |
| 231 | H | H | NHAc | H | H | H | OCO-ringC | H | H | H | H | H | H | H | H | |
| 232 | H | H | Ac | H | H | H | OCO-ringC | H | H | H | H | H | H | H | H | |
| 233 | NO₂ | H | H | H | H | H | OCO-ringC | H | H | H | H | H | H | H | H | |
| 234 | H | NO₂ | H | H | H | H | OCO-ringC | H | H | H | H | H | H | H | H | |
| 235 | H | H | NO₂ | H | H | H | OCO-ringC | H | H | H | H | H | H | H | H | 166-169 |
| 236 | CN | H | H | H | H | H | OCO-ringC | H | H | H | H | H | H | H | H | |
| 237 | H | CN | H | H | H | H | OCO-ringC | H | H | H | H | H | H | H | H | |
| 238 | H | H | CN | H | H | H | OCO-ringC | H | H | H | H | H | H | H | H | |
| 239 | H | H | H | H | H | H | OSO₂-ringC | H | H | H | H | H | Me | H | H | 172-174 |
| 240 | Cl | H | H | H | H | H | OSO₂-ringC | H | H | H | H | H | Me | H | H | 155-156 |
| 241 | H | Cl | H | H | H | H | OSO₂-ringC | H | H | H | H | H | Me | H | H | 192-193 |
| 242 | H | H | Cl | H | H | H | OSO₂-ringC | H | H | H | H | H | Me | H | H | 147-148 |
| 243 | Me | H | H | H | H | H | OSO₂-ringC | H | H | H | H | H | Me | H | H | |
| 244 | H | Me | H | H | H | H | OSO₂-ringC | H | H | H | H | H | Me | H | H | |
| 245 | H | H | Me | H | H | H | OSO₂-ringC | H | H | H | H | H | Me | H | H | |
| 246 | OMe | H | H | H | H | H | OSO₂-ringC | H | H | H | H | H | Me | H | H | |
| 247 | H | OMe | H | H | H | H | OSO₂-ringC | H | H | H | H | H | Me | H | H | |
| 248 | H | H | OMe | H | H | H | OSO₂-ringC | H | H | H | H | H | Me | H | H | 176-177 |
| 249 | H | H | NHAc | H | H | H | OSO₂-ringC | H | H | H | H | H | Me | H | H | |
| 250 | H | H | Ac | H | H | H | OSO₂-ringC | H | H | H | H | H | Me | H | H | |
| 251 | NO₂ | H | H | H | H | H | OSO₂-ringC | H | H | H | H | H | Me | H | H | |
| 252 | H | NO₂ | H | H | H | H | OSO₂-ringC | H | H | H | H | H | Me | H | H | |
| 253 | H | H | NO₂ | H | H | H | OSO₂-ringC | H | H | H | H | H | Me | H | H | 206-207 |
| 254 | CN | H | H | H | H | H | OSO₂-ringC | H | H | H | H | H | Me | H | H | |
| 255 | H | CN | H | H | H | H | OSO₂-ringC | H | H | H | H | H | Me | H | H | |
| 256 | H | H | CN | H | H | H | OSO₂-ringC | H | H | H | H | H | Me | H | H | |
| 257 | H | H | H | H | H | H | OSO₂-ringC | H | H | H | H | H | OMe | H | H | |
| 258 | Cl | H | H | H | H | H | OSO₂-ringC | H | H | H | H | H | OMe | H | H | |
| 259 | H | Cl | H | H | H | H | OSO₂-ringC | H | H | H | H | H | OMe | H | H | |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 260 | H | H | Cl | H | H | H | OSO₂-ringC | H | H | H | H | H | OMe | H | H | |
| 261 | Me | H | H | H | H | H | OSO₂-ringC | H | H | H | H | H | OMe | H | H | |
| 262 | H | Me | H | H | H | H | OSO₂-ringC | H | H | H | H | H | OMe | H | H | |
| 263 | H | H | Me | H | H | H | OSO₂-ringC | H | H | H | H | H | OMe | H | H | |
| 264 | OMe | H | H | H | H | H | OSO₂-ringC | H | H | H | H | H | OMe | H | H | |
| 265 | H | OMe | H | H | H | H | OSO₂-ringC | H | H | H | H | H | OMe | H | H | |
| 266 | H | H | OMe | H | H | H | OSO₂-ringC | H | H | H | H | H | OMe | H | H | |
| 267 | H | H | NHAc | H | H | H | OSO₂-ringC | H | H | H | H | H | OMe | H | H | |
| 268 | H | H | Ac | H | H | H | OSO₂-ringC | H | H | H | H | H | OMe | H | H | |
| 269 | NO₂ | H | H | H | H | H | OSO₂-ringC | H | H | H | H | H | OMe | H | H | |
| 270 | H | NO₂ | H | H | H | H | OSO₂-ringC | H | H | H | H | H | OMe | H | H | |
| 271 | H | H | NO₂ | H | H | H | OSO₂-ringC | H | H | H | H | H | OMe | H | H | |
| 272 | CN | H | H | H | H | H | OSO₂-ringC | H | H | H | H | H | OMe | H | H | |
| 273 | H | CN | H | H | H | H | OSO₂-ringC | H | H | H | H | H | OMe | H | H | |
| 274 | H | H | CN | H | H | H | OSO₂-ringC | H | H | H | H | H | OMe | H | H | |
| 275 | H | H | H | H | H | H | OSO₂-ringC | H | H | H | H | H | Cl | H | H | |
| 276 | Cl | H | H | H | H | H | OSO₂-ringC | H | H | H | H | H | Cl | H | H | |
| 277 | H | Cl | H | H | H | H | OSO₂-ringC | H | H | H | H | H | Cl | H | H | |
| 278 | H | H | Cl | H | H | H | OSO₂-ringC | H | H | H | H | H | Cl | H | H | |
| 279 | Me | H | H | H | H | H | OSO₂-ringC | H | H | H | H | H | Cl | H | H | |
| 280 | H | Me | H | H | H | H | OSO₂-ringC | H | H | H | H | H | Cl | H | H | |
| 281 | H | H | Me | H | H | H | OSO₂-ringC | H | H | H | H | H | Cl | H | H | |
| 282 | OMe | H | H | H | H | H | OSO₂-ringC | H | H | H | H | H | Cl | H | H | |
| 283 | H | OMe | H | H | H | H | OSO₂-ringC | H | H | H | H | H | Cl | H | H | |
| 284 | H | H | OMe | H | H | H | OSO₂-ringC | H | H | H | H | H | Cl | H | H | |
| 285 | H | H | NHAc | H | H | H | OSO₂-ringC | H | H | H | H | H | Cl | H | H | |
| 286 | H | H | Ac | H | H | H | OSO₂-ringC | H | H | H | H | H | Cl | H | H | |
| 287 | NO₂ | H | H | H | H | H | OSO₂-ringC | H | H | H | H | H | Cl | H | H | |
| 288 | H | NO₂ | H | H | H | H | OSO₂-ringC | H | H | H | H | H | Cl | H | H | |
| 289 | H | H | NO₂ | H | H | H | OSO₂-ringC | H | H | H | H | H | Cl | H | H | |
| 290 | CN | H | H | H | H | H | OSO₂-ringC | H | H | H | H | H | Cl | H | H | |
| 291 | H | CN | H | H | H | H | OSO₂-ringC | H | H | H | H | H | Cl | H | H | |
| 292 | H | H | CN | H | H | H | OSO₂-ringC | H | H | H | H | H | Cl | H | H | |
| 293 | H | H | H | H | H | H | H | OCH₂-ringC | H | H | H | H | H | H | H | |
| 294 | Cl | H | H | H | H | H | H | OCH₂-ringC | H | H | H | H | H | H | H | |
| 295 | H | Cl | H | H | H | H | H | OCH₂-ringC | H | H | H | H | H | H | H | |
| 296 | H | H | Cl | H | H | H | H | OCH₂-ringC | H | H | H | H | H | H | H | |

TABLE 1-continued

| Compound No. | ring-A (R¹)n1 | | | | | ring-B (R²)n2 and O-X-ring-C | | | | | Ring-C (R³)n3 | | | | | Melting point (° C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 297 | Me | H | H | H | H | H | H | OCH$_2$-ringC | H | H | H | H | H | H | H | |
| 298 | H | Me | H | H | H | H | H | OCH$_2$-ringC | H | H | H | H | H | H | H | |
| 299 | H | H | Me | H | H | H | H | OCH$_2$-ringC | H | H | H | H | H | H | H | |
| 300 | OMe | H | H | H | H | H | H | OCH$_2$-ringC | H | H | H | H | H | H | H | |
| 301 | H | OMe | H | H | H | H | H | OCH$_2$-ringC | H | H | H | H | H | H | H | |
| 302 | H | H | OMe | H | H | H | H | OCH$_2$-ringC | H | H | H | H | H | H | H | |
| 303 | H | H | NHAc | H | H | H | H | OCH$_2$-ringC | H | H | H | H | H | H | H | |
| 304 | H | H | Ac | H | H | H | H | OCH$_2$-ringC | H | H | H | H | H | H | H | |
| 305 | NO$_2$ | H | H | H | H | H | H | OCH$_2$-ringC | H | H | H | H | H | H | H | |
| 306 | H | NO$_2$ | H | H | H | H | H | OCH$_2$-ringC | H | H | H | H | H | H | H | |
| 307 | H | H | NO$_2$ | H | H | H | H | OCH$_2$-ringC | H | H | H | H | H | H | H | |
| 308 | CN | H | H | H | H | H | H | OCH$_2$-ringC | H | H | H | H | H | H | H | |
| 309 | H | CN | H | H | H | H | H | OCH$_2$-ringC | H | H | H | H | H | H | H | |
| 310 | H | H | CN | H | H | H | H | OCH$_2$-ringC | H | H | H | H | H | H | H | |
| 311 | H | H | H | H | H | H | H | OCO-ringC | H | H | H | H | H | H | H | 215-216 |
| 312 | Cl | H | H | H | H | H | H | OCO-ringC | H | H | H | H | H | H | H | |
| 313 | H | Cl | H | H | H | H | H | OCO-ringC | H | H | H | H | H | H | H | |
| 314 | H | H | Cl | H | H | H | H | OCO-ringC | H | H | H | H | H | H | H | |
| 315 | Me | H | H | H | H | H | H | OCO-ringC | H | H | H | H | H | H | H | |
| 316 | H | Me | H | H | H | H | H | OCO-ringC | H | H | H | H | H | H | H | |
| 317 | H | H | Me | H | H | H | H | OCO-ringC | H | H | H | H | H | H | H | |
| 318 | OMe | H | H | H | H | H | H | OCO-ringC | H | H | H | H | H | H | H | |
| 319 | H | OMe | H | H | H | H | H | OCO-ringC | H | H | H | H | H | H | H | |
| 320 | H | H | OMe | H | H | H | H | OCO-ringC | H | H | H | H | H | H | H | |
| 321 | H | H | NHAc | H | H | H | H | OCO-ringC | H | H | H | H | H | H | H | |
| 322 | H | H | Ac | H | H | H | H | OCO-ringC | H | H | H | H | H | H | H | |
| 323 | NO$_2$ | H | H | H | H | H | H | OCO-ringC | H | H | H | H | H | H | H | |
| 324 | H | NO$_2$ | H | H | H | H | H | OCO-ringC | H | H | H | H | H | H | H | |
| 325 | H | H | NO$_2$ | H | H | H | H | OCO-ringC | H | H | H | H | H | H | H | |
| 326 | CN | H | H | H | H | H | H | OCO-ringC | H | H | H | H | H | H | H | |
| 327 | H | CN | H | H | H | H | H | OCO-ringC | H | H | H | H | H | H | H | |
| 328 | H | H | CN | H | H | H | H | OCO-ringC | H | H | H | H | H | H | H | |
| 329 | H | H | H | H | H | H | H | OSO$_2$-ringC | H | H | H | H | Me | H | H | |
| 330 | Cl | H | H | H | H | H | H | OSO$_2$-ringC | H | H | H | H | Me | H | H | |
| 331 | H | Cl | H | H | H | H | H | OSO$_2$-ringC | H | H | H | H | Me | H | H | |
| 332 | H | H | Cl | H | H | H | H | OSO$_2$-ringC | H | H | H | H | Me | H | H | |
| 333 | Me | H | H | H | H | H | H | OSO$_2$-ringC | H | H | H | H | Me | H | H | |

TABLE 1-continued

| Compound No. | ring-A (R¹)n1 | | | | | ring-B (R²)n2 and O-X-ring-C | | | | | Ring-C (R³)n3 | | | | | Melting point (°C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 334 | H | Me | H | H | H | H | H | OSO$_2$-ringC | H | H | H | H | Me | H | H | |
| 335 | H | H | Me | H | H | H | H | OSO$_2$-ringC | H | H | H | H | Me | H | H | |
| 336 | OMe | H | H | H | H | H | H | OSO$_2$-ringC | H | H | H | H | Me | H | H | |
| 337 | H | OMe | H | H | H | H | H | OSO$_2$-ringC | H | H | H | H | Me | H | H | |
| 338 | H | H | OMe | H | H | H | H | OSO$_2$-ringC | H | H | H | H | Me | H | H | |
| 339 | H | H | NHAc | H | H | H | H | OSO$_2$-ringC | H | H | H | H | Me | H | H | |
| 340 | H | H | Ac | H | H | H | H | OSO$_2$-ringC | H | H | H | H | Me | H | H | |
| 341 | NO$_2$ | H | H | H | H | H | H | OSO$_2$-ringC | H | H | H | H | Me | H | H | |
| 342 | H | NO$_2$ | H | H | H | H | H | OSO$_2$-ringC | H | H | H | H | Me | H | H | |
| 343 | H | H | NO$_2$ | H | H | H | H | OSO$_2$-ringC | H | H | H | H | Me | H | H | |
| 344 | CN | H | H | H | H | H | H | OSO$_2$-ringC | H | H | H | H | Me | H | H | |
| 345 | H | CN | H | H | H | H | H | OSO$_2$-ringC | H | H | H | H | Me | H | H | |
| 346 | H | H | CN | H | H | H | H | OSO$_2$-ringC | H | H | H | H | Me | H | H | |
| 347 | H | H | H | H | H | H | H | OSO$_2$-ringC | H | H | H | H | OMe | H | H | |
| 348 | Cl | H | H | H | H | H | H | OSO$_2$-ringC | H | H | H | H | OMe | H | H | |
| 349 | H | Cl | H | H | H | H | H | OSO$_2$-ringC | H | H | H | H | OMe | H | H | |
| 350 | H | H | Cl | H | H | H | H | OSO$_2$-ringC | H | H | H | H | OMe | H | H | |
| 351 | Me | H | H | H | H | H | H | OSO$_2$-ringC | H | H | H | H | OMe | H | H | |
| 352 | H | Me | H | H | H | H | H | OSO$_2$-ringC | H | H | H | H | OMe | H | H | |
| 353 | H | H | Me | H | H | H | H | OSO$_2$-ringC | H | H | H | H | OMe | H | H | |
| 354 | OMe | H | H | H | H | H | H | OSO$_2$-ringC | H | H | H | H | OMe | H | H | |
| 355 | H | OMe | H | H | H | H | H | OSO$_2$-ringC | H | H | H | H | OMe | H | H | |
| 356 | H | H | OMe | H | H | H | H | OSO$_2$-ringC | H | H | H | H | OMe | H | H | |
| 357 | H | H | NHAc | H | H | H | H | OSO$_2$-ringC | H | H | H | H | OMe | H | H | |
| 358 | H | H | Ac | H | H | H | H | OSO$_2$-ringC | H | H | H | H | OMe | H | H | |
| 359 | NO$_2$ | H | H | H | H | H | H | OSO$_2$-ringC | H | H | H | H | OMe | H | H | |
| 360 | H | NO$_2$ | H | H | H | H | H | OSO$_2$-ringC | H | H | H | H | OMe | H | H | |
| 361 | H | H | NO$_2$ | H | H | H | H | OSO$_2$-ringC | H | H | H | H | OMe | H | H | |
| 362 | CN | H | H | H | H | H | H | OSO$_2$-ringC | H | H | H | H | OMe | H | H | |
| 363 | H | CN | H | H | H | H | H | OSO$_2$-ringC | H | H | H | H | OMe | H | H | |
| 364 | H | H | CN | H | H | H | H | OSO$_2$-ringC | H | H | H | H | OMe | H | H | |
| 365 | H | H | H | H | H | H | H | OSO$_2$-ringC | H | H | H | H | Cl | H | H | |
| 366 | Cl | H | H | H | H | H | H | OSO$_2$-ringC | H | H | H | H | Cl | H | H | |
| 367 | H | Cl | H | H | H | H | H | OSO$_2$-ringC | H | H | H | H | Cl | H | H | |
| 368 | H | H | Cl | H | H | H | H | OSO$_2$-ringC | H | H | H | H | Cl | H | H | |
| 369 | Me | H | H | H | H | H | H | OSO$_2$-ringC | H | H | H | H | Cl | H | H | |
| 370 | H | Me | H | H | H | H | H | OSO$_2$-ringC | H | H | H | H | Cl | H | H | |

TABLE 1-continued

| Compound No. | ring-A (R¹)n1 | | | | | ring-B (R²)n2 and O-X-ring-C | | | | | Ring-C (R³)n3 | | | | | Melting point (° C.) |
|---|---|---|---|---|---|---|---|---|---|---|---|---|---|---|---|---|
| | 2 | 3 | 4 | 5 | 6 | 2 | 3 | 4 | 5 | 6 | 2 | 3 | 4 | 5 | 6 | |
| 371 | H | H | Me | H | H | H | H | OSO$_2$-ringC | H | H | H | H | Cl | H | H | |
| 372 | OMe | H | H | H | H | H | H | OSO$_2$-ringC | H | H | H | H | Cl | H | H | |
| 373 | H | OMe | H | H | H | H | H | OSO$_2$-ringC | H | H | H | H | Cl | H | H | |
| 374 | H | H | OMe | H | H | H | H | OSO$_2$-ringC | H | H | H | H | Cl | H | H | |
| 375 | H | H | NHAc | H | H | H | H | OSO$_2$-ringC | H | H | H | H | Cl | H | H | |
| 376 | H | H | Ac | H | H | H | H | OSO$_2$-ringC | H | H | H | H | Cl | H | H | |
| 377 | NO$_2$ | H | H | H | H | H | H | OSO$_2$-ringC | H | H | H | H | Cl | H | H | |
| 378 | H | NO$_2$ | H | H | H | H | H | OSO$_2$-ringC | H | H | H | H | Cl | H | H | |
| 379 | H | H | NO$_2$ | H | H | H | H | OSO$_2$-ringC | H | H | H | H | Cl | H | H | |
| 380 | CN | H | H | H | H | H | H | OSO$_2$-ringC | H | H | H | H | Cl | H | H | |
| 381 | H | CN | H | H | H | H | H | OSO$_2$-ringC | H | H | H | H | Cl | H | H | |
| 382 | H | H | CN | H | H | H | H | OSO$_2$-ringC | H | H | H | H | Cl | H | H | |

(Recording Material)

A recording material of the present invention can be used for any purpose as long as it is a recording material containing a color former and at least one of the compounds represented by the formula (I), and for example, it can be used as a thermal recording material or a pressure-sensitive copying material.

The proportion of the compound(s) of at least one of the compounds represented by the formula (I) to the color former used is usually 0.01 to 10 parts by mass, preferably 0.5 to 10 parts by mass, and more preferably 1.0 to 5 parts by mass, with respect to 1 part by mass of the color former.

(Other Components in Recording Material)

The recording material of the present invention can contain, in addition to the color former and the compound(s) represented by the formula (I), one or more of color-developing agents, image stabilizers, sensitizers, fillers, dispersants, antioxidants, desensitizers, anti-tack agents, anti-foaming agents, light stabilizers, fluorescent brightening agents, etc., known in the art, as needed. The amount of each of the components used is in the range of usually 0.1 to 15 parts by mass, preferably 1 to 10 parts by mass, with respect to 1 part by mass of the color former.

These agents may be contained in a color-developing layer or may be contained in any layer, for example, a protective layer, when they consist of a multilayer structure. Particularly, when an overcoat layer or an undercoat layer is provided in the upper and/or lower parts of the color-developing layer, these layers can contain antioxidants, light stabilizers, etc. Furthermore, these antioxidants or light stabilizers can be contained in a form encapsulated in microcapsules, as needed, in these layers.

Examples of the color former used in the recording material of the present invention can include, but not limited to, fluoran, phthalide, lactam, triphenylmethane, phenothiazine, and spiropyran leuco dyes. Any color former that forms a color by contact with the color-developing agent, which is an acidic substance, can be used. Moreover, these color formers can be used alone to produce a recording material of the color developed by it, as a matter of course. Alternatively, two or more thereof can be used by mixing. For example, three primary color (red, blue, and green) formers or black color formers can be used by mixing to produce a recording material that develops a true black color.

Examples of the fluoran color formers include 3,3-bis(p-dimethylaminophenyl)phthalide, 3,3-bis(p-dimethylaminophenyl)-6-dimethylaminophthalide (also known as crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluoran, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluoromethylphenyl)amino}-6-diethylaminofluoran, 2-{3,6-bis(diethylamino)-9-(o-chloroanilino)xanthyl}benzoic acid lactam, 3-diethylamino-6-methyl-7-(m-trichloromethylanilino)fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-pyrrolidino-6-methyl-7-anilinofluoran, 3-piperidino-6-methyl-7-anilinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-diethylamino-5-methyl-7-benzylaminofluoran, 3-diethylamino-5-chlorofluoran, 3-diethylamino-6-(N,N'-dibenzylamino)fluoran, 3,6-dimethoxyfluoran, 2,4-dimethyl-6-(4-dimethylaminophenyl)aminofluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-6-methyl-7-(2,4-xylylamino)fluoran, 3-diethylamino-7-(o-fluoroanilino)fluoran, 3-diphenylamino-6-methyl-7-anilinofluoran, benzoylleucomethylene blue, 6'-chloro-8'-methoxy-benzindolino-spiropyran, 6'-bromo-3'-methoxy-benzindolinospiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl)phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-4'-chloro-5'-methylphenyl)phthalide, 3-morpholino-7-(N-propyl-m-trifluoromethylanilino)fluoran, 3-pyrrolidino-7-m-trifluoromethylanilinofluoran, 3-diethylamino-5-chloro-7-(N-benzyl-m-trifluoromethylanilino)fluoran, 3-pyrrolidino-7-di(p-chlorophenyl)aminofluoran, 3-diethylamino-5-chloro-7-(α-phenylethylamino)fluoran, 3-(N-ethyl-p-toluidino)-7-(α-phenylethylamino)fluoran, 3-diethylamino-7-(0-methoxycarbonylphenylamino)fluoran, 3-diethylamino-5-methyl-7-(α-phenylethylamino)fluoran, 3-diethylamino-7-piperidinofluoran, 2-chloro-3-(N-methyltoluidino)-7-(p-n-butylanilino)fluoran, 3-(N-methyl-N-isopropylamino)-6-methyl-7-anilinofluoran, 3-dibutylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-α-naphthylamino-4'-bromofluoran, 3-diethylamino-6-chloro-7-anilinofluoran, 3-N-ethyl-N-(2-ethoxypropyl)amino-6-methyl-7-anilinofluoran, 3-N-ethyl-N-tetrahydrofurfurylamino-6-methyl-7-anilinofluoran, 3-diethylamino-6-methyl-7-mesidino-4',5'-benzofluoran, and 3-(N-ethyl-p-toluidino)-7-(methylphenylamino)fluoran.

Among these color formers, preferable examples thereof can include 3,3-bis(p-dimethylaminophenyl)-6-dimethylaminophthalide, 3-cyclohexylamino-6-chlorofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-diethylamino-7-(o-chloroanilino)fluoran, 3-dibutylamino-7-(o-chloroanilino)fluoran, 3-N-methyl-N-cyclohexylamino-6-methyl-7-anilinofluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-7-(o-fluoroanilino)fluoran, 3-diphenylamino-6-methyl-7-anilinofluoran, benzoylleucomethylene blue, 3-dibutylamino-6-methyl-7-anilinofluoran, 3-N-ethyl-N-tetrahydrofurfurylamino-6-methyl-7-anilinofluoran, and 3-(N-ethyl-p-toluidino)-7-(methylphenylamino)fluoran.

Moreover, examples of near infrared absorbing dyes include 3-[4-[4-(4-anilino)-anilino]anilino]-6-methyl-7-chlorofluoran, 3,3-bis[2-(4-dimethylaminophenyl)-2-(4-methoxyphenyl)vinyl]-4,5,6,7-tetrachlorophthalide, and 3,6,6'-tris(dimethylamino)spiro(fluorene-9,3'-phthalide).

At least one of the compounds represented by the formula (I) of the present invention is suitably used as a color-developing agent mainly in a thermal recording material, and these compounds alone can be used or these compounds can be used together with a plurality of known color-developing agents. The ratio among them is arbitrary.

Examples of other color-developing agents can specifically include the followings:

bisphenol compounds such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl)hexane, 2,2-bis(4-hydroxyphenyl)propane, 2,2-bis(4-hydroxyphenyl)butane, 2,2-bis(4-hydroxy-3-methylphenyl)propane, 4,4'-(1-phenylethylidene)bisphenol, 4,4'-ethylidenebisphenol, (hydroxyphenyl)methylphenol, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and butyl 2,2-bis(4-hydroxyphenyl)acetate; sulfur-containing bisphenol compounds such as 4,4'-dihydroxydiphenyl thioether, 1,7-di(4-hydroxyphenylthio)-3,5-dioxaheptane, 2,2'-bis(4-hydroxyphenylthio)diethyl ether, and 4,4'-dihydroxy-3,3'-dimethyldiphenyl thioether; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, and diphenylmethyl 4-hydroxybenzoate; metal salts of benzoic acid such as zinc benzoate and zinc 4-nitrobenzoate, and salicylic acids such as 4-[2-(4-methoxyphenyloxy)ethyloxy]salicylic acid; metal salts of salicylic acid such as zinc salicylate and zinc bis[4-(octyloxycarbonylamino)-2-hydroxybenzoate];

hydroxysulfones such as 4,4'-dihydroxydiphenylsulfone (abbreviated as 4,4'-BPS), 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 4-allyloxy-4'-hydroxydiphenylsulfone, 2-(4-hydroxyphenylsulfonyl)phenol, 4,4'-sulfonylbis[2-(2-propenyl)]phenol, 4-[[4-(propoxy)phenyl}sulfonyl]phenol, 4-[{4-(allyloxy)phenyl}sulfonyl]phenol, 4-[{4-(benzyloxy)phenyl}sulfonyl]phenol, and bis(phenylsulfonyl)-5-methylphenol; polyvalent metal salts of hydroxysulfones such as 4-phenylsulfonylphenoxy-zinc magnesium, -aluminum, and -titanium; 4-hydroxyphthalic acid diesters such as dimethyl 4-hydroxyphthalate, dicyclohexyl 4-hydroxyphthalate, and diphenyl 4-hydroxyphthalate; hydroxynaphthoic acid esters such as 2-hydroxy-6-carboxynaphthalene; trihalomethylsulfones such as tribromomethylphenylsulfone; sulfonamide compounds such as N-phenyl-4-aminobenzenesulfonamide, N-phenyl-3-nitrobenzenesulfonamide, N-(2-methoxyphenyl)-p-toluenesulfonamide, and Neo-Uliron; diphenylurea compounds such as 1,2-diphenylurea, N-phenyl-4-(3-phenylureido)benzenesulfonamide, 4-methyl-N-(2-(3-phenylureido)phenyl)benzenesulfonamide, N-(2-(3-phenylureido) phenyl)benzenesulfonamide, N-(2-(3-phenylureido)phenyl) acetamide, and 4-methyl-N-(2-(3-phenylureido)phenyl) benzamide; sulfonylurea compounds such as 4,4'-bis(p-toluenesulfonylaminocarbonylamino)diphenylmethane, and N-(4-methylphenylsulfonyl)-N'-(3-(4-methylphenylsulfonyloxy)phenyl)urea (abbreviated as PF-201); hydroxyacetophenone, p-phenylphenol, benzyl 4-hydroxyphenylacetate, p-benzylphenol, hydroquinone-monobenzyl ether, 2,4-dihydroxy-2'-methoxybenzanilide, tetracyanoquinodimethanes, N-(2-hydroxyphenyl)-2-[(4-hydroxyphenyl)thio]acetamide, N-(4-hydroxyphenyl)-2-[(4-hydroxyphenyl)thio]acetamide, 4-hydroxybenzenesulfonanilide, 4'-hydroxy-4-methylbenzenesulfonanilide, 4,4'-bis(4-methyl-3-phenoxycarbonyl) aminophenylureido))diphenylsulfone, 3-(3-phenylureido) benzenesulfonanilide, octadecylphosphoric acid, and dodecylphosphoric acid; and cross-linked diphenylsulfone compounds represented by the following formula or mixtures thereof:

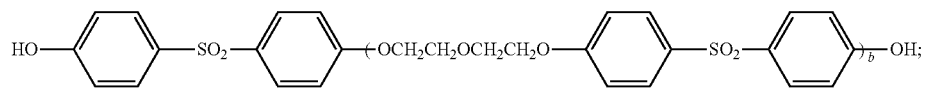

Among them, preferable examples thereof include 4-hydroxy-4'-isopropoxydiphenylsulfone, cross-linked diphenylsulfone compounds or mixtures thereof, and N-(2-(3-phenylureido)phenyl)benzenesulfonamide.

Examples of the image stabilizer can include: epoxy group-containing diphenylsulfones such as 4-benzyloxy-4'-(2-methylglycidyloxy)-diphenylsulfone and 4,4'-diglycidyloxydiphenylsulfone; 1,4-diglycidyloxybenzene, 4-[α-(hydroxymethyl)benzyloxy]-4'-hydroxydiphenylsulfone, 2-propanol derivatives, salicylic acid derivatives, metal salts (particularly, zinc salts) of oxynaphthoic acid derivatives, metal salts of 2,2-methylenebis(4,6-t-butylphenyl)phosphate, and other water-insoluble zinc compounds; hindered phenol compounds such as 2,2-bis(4'-hydroxy-3',5'-dibromophenyl)propane, 4,4'-sulfonylbis(2,6-dibromophenol), 4,4'-butylidene(6-t-butyl-3-methylphenol), 2,2'-methylenebis(4-methyl-6-t-butylphenol), 2,2'-methylene-bis(4-ethyl-6-t-butylphenol), 2,2'-di-t-butyl-5,5'-dimethyl-4,4'-sulfonyldiphenol, 1,1,3-tris(2-methyl-4-hydroxy-5-cyclohexylphenyl)butane, and 1,1,3-tris(2-methyl-4-hydroxy-5-t-butylphenyl)butane, and phenol novolac compounds, epoxy resins, UU (color-developing agent manufactured by CHEMIPRO KASEI Kaisha, Ltd.), 3,3'-diaminodiphenylsulfone, and 4,4'-diaminodiphenylsulfone.

The examples further include a cross-linked diphenylsulfone compound represented by the following formula or a mixture thereof:

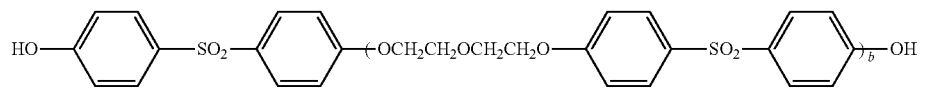

The image stabilizer is preferably a compound that is solid at room temperature, particularly preferably has a melting point of 60° C. or higher, and is poorly soluble in water.

Examples of the sensitizer can include: higher fatty acid amides such as stearic acid amide, stearic acid anilide, and palmitic acid amide; amides such as benzamide, acetoacetic acid anilide, thioacetanilide acrylic acid amide, ethylenebisamide, ortho-toluenesulfonamide, and para-toluenesulfonamide; phthalic acid diesters such as dimethyl phthalate, dibenzyl isophthalate, dimethyl isophthalate, dimethyl terephthalate, diethyl isophthalate, diphenyl isophthalate, and dibenzyl terephthalate; oxalic acid diesters such as dibenzyl oxalate, di(4-methylbenzyl) oxalate, di(4-chlorobenzyl) oxalate, a mixture of equal parts of dibenzyl oxalate and di(4-chlcrobenzyl) oxalate, and a mixture of equal parts of di(4-chlorobenzyl) oxalate and di(4-methylbenzyl) oxalate; bis(t-butylphenols) such as 2,2'-methylenebis(4-methyl-6-t-butylphenol) and 4,4'-methylene-bis-2,6-di-t-butylphenol; 4,4'-dihydroxydiphenylsulfone diethers such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone, and 4,4'-diallyloxydiphenylsulfone; 2,4'-dihydroxydiphenylsulfone diethers such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, 2,4'-dihexyloxydiphenylsulfone, and 2,4'-diallyloxydiphenylsulfone; 1,2-bis(phenoxy)ethane, 1,2-bis(4-methylphenoxy)ethane, 1,2-bis(3-methylphenoxy)ethane, 1,2-bis(phenoxymethyl)benzene, 1,2-bis(4-methoxyphenylthio)ethane, 1,2-bis(4-methoxyphenoxy) propane, 1,3-diphenoxy-2-propanol, 1,4-diphenylthio-2-butene, 1,4-diphenylthiobutane, 1,4-diphenoxy-2-butene, 1,5-bis(4-methoxyphenoxy)-3-oxapentane, 1,3-dibenzoyloxypropane, dibenzoyloxymethane, 4,4'-ethylenedioxy-bis-benzoic acid dibenzyl ester, bis[2-(4-methoxy-phenoxy)ethyl] ether, 2-naphthylbenzyl ether, 1,3-bis(2-vinyloxyethoxy)benzene, 1,4-diethoxynaphthalene, 1,4-dibenzyloxynaphthalene, 1,4-dimethoxynaphthalene, 1,4-bis(2-vinyloxyethoxy)benzene, p-(2-vinyloxyethoxy)biphenyl, p-aryloxybiphenyl, p-propargyloxybiphenyl, p-benzyloxybenzyl alcohol, 4-(m-methylphenoxymethyl)biphenyl, 4-methylphenyl-biphenyl ether, di-β-naphthylphenylenediamine, diphenylamine, carbazole, 2,3-di-m-tolylbutane, 4-benzylbiphenyl, 4,4'-dimethylbiphenyl, terphenyls such as m-terphenyl and p-terphenyl; 1,2-bis(3,4-dimethylphenyl)ethane, 2,3,5,6-tetramethyl-4'-methyldiphenylmethane, 4-acetylbiphenyl, dibenzoylmethane, triphenylmethane, phenyl 1-hydroxy-naphthoate, methyl 1-hydroxy-2-naphthoate, N-octadecylcarbamoyl-p-methoxycarbonylbenzene, benzyl p-benzyloxybenzoate, phenyl β-naphthoate, methyl p-nitrobenzoate, diphenylsulfone, carbonic acid derivatives such as diphenyl carbonate, guaiacol carbonate, di-p-tolyl carbonate, and phenyl-α-naphthyl carbonate; 1,1-diphenylpropanol, 1,1- diphenylethanol, diphenylmethanol, N-octadecylcarbamoylbenzene, dibenzyl disulfide, N,N'-1,2-phenylenebis(3-phenylurea), stearic acid, Amide AP-1(7:3 mixture of stearic acid amide and palmitic acid amide), stearates such as aluminum stearate, calcium stearate, and zinc stearate; and zinc palmitate, behenic acid, zinc behenate, montanic acid wax, and polyethylene wax.

Preferable examples thereof can include 2-naphthylbenzyl ether, m-terphenyl, 4-benzylbiphenyl, benzyl oxalate, di(4-chlorobenzyl) oxalate, a mixture of equal parts of benzyl oxalate and di(4-chlorobenzyl) oxalate, di(4-methylbenzyl) oxalate, a mixture of equal parts of di(4-chlorobenzyl) oxalate and di(4-methylbenzyl) oxalate, phenyl 1-hydroxy-2-naphthoate, 1,2-bis(phenoxy)ethane, 1,2-bis(3-methylphenoxy)ethane, 1,2-bis(phenoxymethyl)benzene, N,N'-1,2-phenylenebis(3-phenylurea), dimethyl terephthalate, stearic acid amide, Amide AP-1(7:3 mixture of stearic acid amide and palmitic acid amide), diphenylsulfone, and 4-acetylbiphenyl.

More preferable examples thereof can include di(4-methylbenzyl) oxalate, 1,2-bis(3-methylphenoxy)ethane, 1,2-bis(phenoxymethyl)benzene, diphenylsulfone, and 2-naphthylbenzyl ether.

Examples of the filler can include silica, clay, kaolin, calcinated kaolin, talc, satin white, aluminum hydroxide, calcium carbonate, magnesium carbonate, zinc oxide, titanium oxide, barium sulfate, magnesium silicate, aluminum silicate, plastic pigments, diatomaceous earth, talc, and aluminum hydroxide. Among them, preferable examples thereof can include calcinated kaolin and calcium carbonate. The ratio of the filler used is 0.1 to 15 parts by mass, preferably 1 to 10 parts by mass, with respect to 1 part by mass of the color former. Moreover, these fillers may be used by mixing.

Examples of the dispersant can include: polyvinyl alcohols having various degrees of saponification and polymerization, such as polyvinyl alcohol, acetoacetylated polyvinyl alcohol, carboxy-modified polyvinyl alcohol, sulfonic acid-modified polyvinyl alcohol, amide-modified polyvinyl alcohol, and butyral-modified vinyl alcohol; cellulose derivatives such as methylcellulose, carboxymethylcellulose, hydroxyethylcellulose, ethylcellulose, acetylcellulose, and hydroxymethylcellulose; and sodium polyacrylate; polyacrylic acid ester; polyacrylamide; starch; sulfosuccinic acid esters such as dioctyl sodium sulfosuccinate; sodium dodecylbenzenesulfonate; a sodium salt of lauryl alcohol sulfuric acid ester, fatty acid salt; styrene-maleic anhydride copolymers; styrene-butadiene copolymers; polyvinyl chloride; polyvinyl acetate; polyacrylic acid ester; polyvinylbutyral; polyurethane; polystyrene and copolymers thereof; polyamide resins; silicone resins; petroleum resins; terpene resins; ketone resins; and coumarone resins.

The dispersant is used in a state of solution dissolved in a solvent such as water, alcohol, ketone, ester, or hydrocarbon. Alternatively, the dispersant may be used in a state emulsified in water or other solvents or in the form of paste dispersed therein.

Examples of the antioxidant can include 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, tris(2-methyl-4-hydroxy-5-cyclohexylphenyl)butane, methylenebis(6-t-butyl-4-methylphenol), methylenebis(6-t-butyl-4-ethylphenol), 4,4'-thiobis(6-t-butyl-3-methylphenol), 1,3,5-tris[{4-(1,1-dimethylethyl)-3-hydroxy-2,6-dimethylphenyl}methyl]-1,3,5-triazine-2,4,6(1H,3H,5H)-trione, and 1,3,5-tris[{3,5-bis(1,1-dimethylethyl)-4-hydroxyphenyl}methyl]-1,3,5-triazine-2,4,6(1H,3H,5H)-trione.

Examples of the desensitizer can include aliphatic higher alcohols, polyethylene glycol, and guanidine derivatives.

Examples of the anti-tack agent can include stearic acid, zinc stearate, calcium stearate, carnauba wax, paraffin wax, and ester wax.

Examples of the antifoaming agent can include higher alcohol-based, fatty acid ester-based, oil-based, silicone-based, polyether-based, modified hydrocarbon-based, and paraffin-based antifoaming agents.

Examples of the light stabilizer can include: salicylic acid-based UV absorbers such as phenyl salicylate, p-t-butylphenyl salicylate, and p-octylphenyl salicylate; benzophenone-based UV absorbers such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane; benzotriazole-based UV absorbers such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-tert-butylphenyl)benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, 2,2'-methylenebis[4-(1,1,3,3-tetramethylbutyl)-6-(2H-benzotriazol-2-yl)]phenol, and a condensate of polyethylene glycol and methyl-3-[3-t-butyl-5-(2H-benzotriazol-2-yl)-4-hydroxyphenyl]propionate; cyanoacrylate-based UV absorbers such as 2'-ethylhexyl-2-cyano-3,3-diphenylacrylate and ethyl-2-cyano-3,3-diphenylacrylate; hindered amine-based UV absorbers such as bis(2,2,6,6-tetramethyl-4-piperidyl)sebacate, succinic acid-bis(2,2,6,6-tetramethyl-4-piperidyl) ester, and 2-(3,5-di-t-butyl)malonic acid-bis(1,2,2,6,6-pentamethyl-4-piperidyl) ester; and 1,8-dihydroxy-2-acetyl-3-methyl-6-methoxynaphthalene.

Examples of the fluorescent brightening agent can include 4,4'-bis[2-anilino-4-(2-hydroxyethyl)amino-1,3,5-triazinyl-6-amino]stilbene-2,2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-anilino-4-bis(hydroxypropyl)amino-1,3,5-triazinyl-6-amino]stilbene-2,2'-disulfonic acid disodium salt, 4,4'-bis[2-methoxy-4-(2-hydroxyethyl)amino-1,3,5-triazinyl-6-amino]stilbene-2,2'-disulfonic acid disodium salt, 4,4'-bis[2-methoxy-4-(2-hydroxypropyl)amino-1,3,5-triazinyl-6-amino]stilbene-2,2'-disulfonic acid disodium salt, 4,4'-bis[2-m-sulfoanilino-4-bis(hydroxyethyl)amino-1,3,5-triazinyl-6-amino]stilbene-2,2'-disulfonic acid disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-triazinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt.

(Method for Producing Recording Material)

When the present invention is used in thermal recording paper, it may be used in the same way as a known use method. For example, the thermal recording paper can be produced by separately dispersing fine particles of the compound of the present invention and fine particles of a color former in aqueous solutions of water-soluble binders such as polyvinyl alcohol or cellulose, mixing these suspension solutions, applying the mixture to a support such as paper, and drying it.

The production method of pressure-sensitive copying paper using the present invention is the same as the production method using a known color-developing agent or sensitizer. For example, a color former microencapsulated by a known method is dispersed with an appropriate dispersant and applied to paper to prepare a sheet of the color former. Moreover, a dispersion solution of a color-developing agent is applied to paper to prepare a sheet of the color-developing agent. Both the sheets thus prepared are combined to prepare pressure-sensitive copying paper. The pressure-sensitive copying paper may be a unit consisting of: upper paper carrying a microcapsule containing a solution of a color former in an organic solvent, wherein the microcapsule is applied and carried on the underside of the upper paper; and lower paper carrying a color-developing agent (acidic substance) applied and carried on the top surface of the lower paper. Alternatively, the pressure-sensitive copying paper may be so-called self-contained paper comprising the microcapsule and the color-developing agent applied on the same paper surface.

Examples of the color-developing agent used in the production or the color-developing agent mixed with the compound of the present invention, which is conventionally known, can include: inorganic acidic substances such as acid white clay, activated white clay, attapulgite, bentonite, colloidal silica, aluminum silicate, magnesium silicate, zinc silicate, tin silicate, calcinated kaolin, and talc; aliphatic carboxylic acids such as oxalic acid, maleic acid, tartaric acid, citric acid, succinic acid, and stearic acid; aromatic carboxylic acids such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3,5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid, and 2-hydroxy-1-benzyl-3-naphthoic acid, and metal salts thereof such as zinc, magnesium, aluminum, and titanium; phenol resin-based color-developing agents such as p-phenylphenol-formalin resins and p-butylphenol-acetylene resins, and mixtures of these phenol resin-based color-developing agents and the metal salts of the aromatic carboxylic acids.

The conventionally known paper such as a synthetic paper, a film, a plastic film, a foamed plastic film, nonwoven cloth, recycled paper produced by recycled paper pulps) can be used as the support used in the present invention. Moreover, the combination thereof can also be used as the support.

If paper is used as the support, a dispersion solution containing a dispersion solution of a color former, a dispersion solution of a color-developing agent, and a dispersion solution of a filler can be directly applied to the paper, or the dispersion solution can be applied after applying a dispersion solution for an undercoat layer to the paper and drying it. Preferably, the dispersion solution for the undercoat layer is applied before applying the dispersion solution because better color-developing sensitivity is thus attained.

The dispersion solution for the undercoat layer is used for improving the smoothness on the surface of the support and is not particularly limited, but preferably contains a filler, a dispersant and water, and specifically, calcinated kaolin or calcium carbonate is preferred as the filler, and polyvinyl alcohol is preferred as the dispersant.

Examples of methods for forming a recording material layer on the support include a method comprising applying a dispersion solution containing a dispersion solution of a color former, a dispersion solution of a color-developing agent, and a dispersion solution of a filler to a support, followed by drying, a method comprising spraying such a dispersion solution onto a support with a spray or the like, followed by drying, and a method comprising dipping a support in such a dispersion solution for a given time, followed by drying. Moreover, examples of the application method include hand coating, a size press coater method, a roll coater method, an air knife coater method, a blend coater method, a flow coater method, a curtain coater method, a comma direct method, a gravure direct method, a gravure reverse method, and a reverse roll coater method.

EXAMPLES

Hereinafter, a recording material of the present invention is described in detail with reference to Examples. However, the present invention is not necessarily limited to them.

Incidentally, Ansilex(R)-93 was used as the calcinated kaolin.

(1) Synthesis of Compounds

Each compound was synthesized by any of the methods described in the paragraphs of (Method for producing compound represented by formula (I)).

[Example 1] Synthesis of 1-(2-(benzyloxy)phenyl)-3-phenylurea (Compound No. 1)

To 200 ml of acetonitrile, 10.9 g of o-aminophenol was added, and the resultant was cooled to 5° C. To this solution, 11.9 g of phenyl isocyanate (manufactured by Wako Pure Chemical Industries, Ltd., purity 98%) was added dropwise while preventing the temperature from increasing to 10° C. or more, and then, a reaction was performed at the same temperature for 30 minutes. After the completion of the reaction, the thus deposited crystals were filtered off to obtain 1-(2-hydroxyphenyl)-3-phenylurea as white crystals (19.5 g, yield 85%).

To 15 ml of DMF, 3.4 g of the 1-(2-hydroxyphenyl)-3-phenylurea obtained as described above and 7.0 g of a 10% sodium hydroxide aqueous solution were added. To the resultant, 2.1 g of benzyl chloride was added dropwise at room temperature, and a reaction was performed at room temperature for 4 hours, and further at 60° C. for 3 hours. After the completion of the reaction, the temperature was restored to room temperature, 50 ml of ethyl acetate and 20 ml of n-hexane were added thereto, and the thus deposited crystals were filtered off. The resultant was dried under reduced pressure to obtain the title compound as white crystals (2.2 g, yield 47%). Melting point: 172-173° C.

[Example 2] Synthesis of 2-(3-phenylureido)phenyl benzoate (Compound No. 67)

To 50 ml of acetone, 3.0 g of 1-(2-(hydroxyphenyl)-3-phenylurea, that is, a synthetic intermediate obtained in the same manner as in Example 1, and 2.0 g of triethylamine were added. To this solution, 1.8 g of benzoyl chloride was added dropwise at 40° C., and a reaction was performed for 2 hours. After the completion of the reaction, an insoluble substance was removed by filtering, and the solvent was distilled off under reduced pressure. The residue was recrystallized from 75 ml of 66% ethanol. The thus deposited crystals were filtered off and dried under reduced pressure to obtain the title compound as white crystals (3.7 g, yield 98%). Melting point: 171-174° C.

[Example 3] Synthesis of 1-(3-benzyloxy)phenyl)-3-phenylurea (Compound No. 203)

To 200 ml of acetonitrile, 10.9 g of m-aminophenol was added, and the resultant was cooled to 5° C. To this solution, 11.9 g of phenyl isocyanate was added dropwise while preventing the temperature from increasing to 10° C. or more, and then, a reaction was performed at the same temperature for 30 minutes. After the completion of the reaction, the thus deposited crystals were filtered off to obtain 1-(3-hydroxyphenyl)-3-phenylurea as white crystals (19.5 g, yield 85%).

To 20 ml of DMF, 4.6 g of the 1-(3-hydroxyphenyl)-3-phenylurea obtained as described above and 1.4 g of potassium carbonate were added, and the resultant was heated to 90° C. in an oil bath. To the resultant, 2.5 g of benzyl chloride was added dropwise, and a reaction was performed at 90° C. for 2 hours. After the completion of the reaction, the reaction solution was added dropwise to 100 ml of 1% hydrochloric acid, and the thus deposited crystals were filtered off. To the resultant crystals, 120 ml of ethyl acetate was added to dissolve the crystals therein under reflux. To the resultant, n-hexane was added, the resultant was cooled to room temperature, and the thus deposited crystals were filtered off. The resultant was dried under reduced pressure to obtain the title compound as white crystals (3.7 g, yield 58%). Melting point: 179-182° C.

[Example 4] Synthesis of 3-(3-phenylureido)phenyl benzoate (Compound No. 221)

To 100 ml of acetonitrile, 4.6 g of 1-(3-(hydroxyphenyl)-3-phenylurea, that is, a synthetic intermediate obtained in the same manner as in Example 3, and 2.0 g of triethylamine were added. To this solution, 2.8 g of benzoyl chloride was added dropwise at room temperature, and a reaction was performed at the same temperature for 1 hour. After the completion of the reaction, the solvent was distilled off under reduced pressure, and the residue was dissolved in 100 ml of ethyl acetate and washed with 100 ml of 5% hydrochloric acid. After separation, an organic layer was dried over magnesium sulfate. The solvent was distilled off under reduced pressure, and the residue was recrystallized from acetone. The thus obtained crystals were filtered off and dried under reduced pressure to obtain the title compound as white crystals (4.0 g, yield 60%). Melting point: 174-179° C.

[Example 5] Synthesis of 3-(3-phenylureido)phenyl-4-methylbenzenesulfonate (Compound No. 239)

To 50 ml of acetone, 4.6 g of 1-(3-hydroxyphenyl)-3-phenylurea, that is, a synthesis intermediate obtained in the same manner as in Example 3, and 2.1 g of triethylamine were added. To this solution, 4.0 g of p-toluenesulfonyl chloride was added, and a reaction was performed at room temperature for 3 hours. After the completion of the reaction, 1% hydrochloric acid was added to the reaction solution, and the thus deposited crystals were filtered off. The thus obtained crystals were well washed with water, and dried under reduced pressure to obtain the title compound as white crystals (7.0 g, yield 91%). Melting point: 172-174° C.

[Example 6] Synthesis of 4-(3-phenylureido)phenyl benzoate (Compound No. 311)

To 50 ml of ethyl acetate, 5.5 g of p-aminophenol was added, and the resultant was cooled to 5° C. To this solution, 6.0 g of phenyl isocyanate was added dropwise while preventing the temperature from increasing to 10° C. or more, and then, a reaction was performed at the same temperature for 1 hour. After the completion of the reaction, the thus deposited crystals were filtered off, and added to 100 ml of acetone. To the resultant, 7.0 g of benzoyl chloride was added dropwise at 40° C., and a reaction was performed for 30 minutes. After the completion of the reaction, the solvent was distilled off under reduced pressure to obtain the title compound as white crystals (12.6 g, yield 75%). Melting point: 215-216° C.

(2) Preparation and Test of Thermal Recording Paper
1) Preparation of Thermal Recording Paper
[Evaluation Sample 3]

| Dispersion solution of color former (solution A) | |
| --- | --- |
| 3-Di-n-butylamino-6-methyl-7-anilinofluoran | 16 parts |
| 10% Aqueous solution of polyvinyl alcohol | 84 parts |
| Dispersion solution of color-developing agent (solution B) | |
| Compound No. 1 (see Table 1) | 16 parts |
| 10% Aqueous solution of polyvinyl alcohol | 84 parts |
| Dispersion solution of filler (solution C) | |
| Calcinated kaolin | 27.8 parts |
| 10% Aqueous solution of polyvinyl alcohol | 26.2 parts |
| Water | 71 parts |

(parts: parts by mass)

Each mixture having the composition of the solution A, B, or C was sufficiently ground with a sand grinder to prepare dispersion solutions of the components of the solutions A to C, and 1 part by mass of the solution A, 2 parts by mass of the solution B, and 4 parts by mass of the solution C were mixed to prepare a coating solution. This coating solution was applied to white paper using a wire rod (manufactured by Webster, Wire Bar No. 12), the paper was dried, and then, calendering treatment was performed to prepare thermal recording paper (coating solution: approximately 5.5 g/m² in terms of dry mass).

[Evaluation Samples 4 to 24]

Thermal paper was prepared in the same manner as described with respect to the evaluation sample 3 above except that each compound shown in Table 1 was used instead of the compound No. 1 in the dispersion solution of the color-developing agent (solution B) of the evaluation sample 3. The relationship between the evaluation sample No. and the color-developing agent is shown in Table 2.

[Evaluation Samples 1 and 2]

Thermal paper was prepared in the same manner as described with respect to the evaluation sample 3 above except that P-201 (evaluation sample 1) or 4,4'-BPS (evaluation sample 2) was used instead of the compound No. 1 in the dispersion solution of the color-developing agent (solution B) of the evaluation sample 3. The relationship between the evaluation sample No. and the color-developing agent is shown in Table 2.

Here, P-201 means N-p-toluenesulfonyl-N'-3-(p-toluenesulfonyloxyphenyl)urea, and 4,4'-BPS means 4,4'-dihydroxydiphenylsulfone.

2) Saturated Color Development Test

In each thermal recording paper prepared as the evaluation samples 1 to 24, saturated color development was caused in a checkered pattern by using a thermal printing tester (manufactured by Ohkura Electric Co., Ltd., Model TH-PMD) under conditions of a printing voltage of 17 V and a pulse width of 1.8 ms. The optical concentration attained after the color development was measured by a spectrophotometer (Spectroeye LT, manufactured by X-rite). The results are shown in Table 2.

TABLE 2

RESULTS OF SATURATED COLOR DEVELOPMENT TEST

| EVALUATION SAMPLE | COLOR-DEVELOPING AGENT | SATURATED CONCENTRATION |
| --- | --- | --- |
| 1 | P-201 | 1.21 |
| 2 | 4,4'-BPS | 1.17 |
| 3 | No. 1 | 0.89 |
| 4 | No. 4 | 1.02 |
| 5 | No. 67 | 0.91 |
| 6 | No. 70 | 0.82 |
| 7 | No. 149 | 0.96 |
| 8 | No. 152 | 0.96 |
| 9 | No. 203 | 1.26 |
| 10 | No. 204 | 1.20 |
| 11 | No. 205 | 1.26 |
| 12 | No. 206 | 1.27 |
| 13 | No. 221 | 1.25 |
| 14 | No. 222 | 1.12 |
| 15 | No. 223 | 1.23 |
| 16 | No. 224 | 1.13 |
| 17 | No. 235 | 1.17 |
| 18 | No. 239 | 1.22 |
| 19 | No. 240 | 1.19 |
| 20 | No. 241 | 1.21 |
| 21 | No. 242 | 1.25 |
| 22 | No. 248 | 1.23 |
| 23 | No. 253 | 1.09 |
| 24 | No. 311 | 1.06 |

It was revealed from the results shown in Table 2 that the compounds of the present invention used together with a color former show good color development which is comparable to that of P-201 and 4,4'-BPS, that is, a conventionally used color-developing agent.

3) Background Heat Resistance Test

Each test paper of the evaluation samples 1 to 24 was subjected to a storage property test under conditions shown below before and after a test. The results are summarized in Table 3.

[Before Test]

A portion of each thermal recording paper prepared as the evaluation samples 1 to 24 was cut off, and the optical concentration of the background was measured by the spectrophotometer (Spectroeye LT, manufactured by X-rite). The results are shown in Table 3.

[Heat Resistance Test]

A portion of each thermal recording paper prepared as the evaluation samples 1 to 24 was cut off and kept in a thermostat (trade name: DK-400, manufactured by Yamato Scientific Co., Ltd.) at a temperature of 100° C. for 24 hours. The optical concentration of the background after thus being kept was measured by the spectrophotometer (Spectroeye LT, manufactured by X-rite). The results are shown in Table 3.

TABLE 3

RESULTS OF BACKGROUND HEAT RESISTANCE TEST

| EVALUATION SAMPLE | BEFORE TEST | BACKGROUND HEAT RESISTANCE 100° C. 24 hours |
| --- | --- | --- |
| 1 | 0.11 | 0.21 |
| 2 | 0.11 | 0.13 |
| 3 | 0.07 | 0.08 |
| 4 | 0.07 | 0.07 |
| 5 | 0.07 | 0.08 |
| 6 | 0.07 | 0.07 |
| 7 | 0.07 | 0.08 |
| 8 | 0.07 | 0.09 |
| 9 | 0.07 | 0.10 |
| 10 | 0.05 | 0.07 |
| 11 | 0.09 | 0.12 |
| 12 | 0.08 | 0.10 |
| 13 | 0.08 | 0.13 |
| 14 | 0.05 | 0.06 |
| 15 | 0.09 | 0.09 |
| 16 | 0.08 | 0.10 |
| 17 | 0.08 | 0.11 |
| 18 | 0.07 | 0.10 |
| 19 | 0.06 | 0.09 |
| 20 | 0.06 | 0.08 |
| 21 | 0.14 | 0.61 |
| 22 | 0.05 | 0.07 |
| 23 | 0.06 | 0.08 |
| 24 | 0.07 | 0.08 |

On the basis of Table 3, the recording materials of the present invention were free from background fogging. Besides, it was revealed that the recording materials of the present invention are excellent in the background heat resistance.

4) Image Storage Property Test

Each test paper of the evaluation samples 1, 2, 8, 11 to 13, 15, 17 to 21 and 23 was subjected to a storage property test under conditions shown below. The evaluation made on the basis of the test results is summarized in Table 4.

[Before Test]

A portion of each thermal recording paper prepared as the evaluation samples 1, 2, 8, 11 to 13, 15, 17 to 21 and 23 was cut off and colored under conditions of a printing voltage of 17 V and a pulse width of 1.8 ms by using the thermal printing tester (trade name: model TH-PMH, manufactured by Ohkura Electric Co., Ltd.), and the concentration of the colored image was measured by the spectrophotometer (Spectroeye LT, manufactured by X-rite). The results are shown in Table 4.

[Heat Resistance Test]

A portion of each thermal recording paper prepared as the evaluation samples 1, 2, 8, 11 to 13, 15, 17 to 21 and 23 was cut off, and the saturated color development was caused in the same manner as before the test. Subsequently, each test paper was kept in the thermostat (trade name: DK-400, manufactured by Yamato Scientific Co., Ltd.) at a temperature of 100° C. for 24 hours. The optical concentration of the background after thus being kept was measured by the spectrophotometer (Spectroeye LT, manufactured by X-rite). The results are shown in Table 4.

[Plasticizer Resistance Test]

A portion of each thermal recording paper prepared as the evaluation samples 1, 2, 8, 11 to 13, 15, 17 to 21 and 23 was cut off, and the saturated color development was caused in the same manner as before the test. Subsequently, a vinyl chloride wrapping film (one containing a plasticizer) was brought into close contact with the color-developed surface and the other surface of each test paper, and the test paper was kept in that state at 40° C. for 4 hours. After the test, the optical concentration was measured by the spectrophotometer (Spectroeye LT, manufactured by X-rite). The results are shown in Table 4.

[Alcohol Resistance Test]

A portion of each thermal recording paper prepared as the evaluation samples 1, 2, 8, 11 to 13, 15, 17 to 21 and 23 was cut off, and the saturated color development was caused in the same manner as before the test. Subsequently, each test paper was dipped in a 35% ethanol solution at 25° C. for 1 hour. After the test, the optical concentration was measured by the spectrophotometer (Spectroeye LT, manufactured by X-rite). The results are shown in Table 4.

TABLE 4

RESULTS OF IMAGE STABILITY

| EVALUATION SAMPLE | IMAGE HEAT RESISTANCE (%) 100° C. 24 hours | PLASTICIZER RESISTANCE (%) | ALCOHOL RESISTANCE (%) |
|---|---|---|---|
| 1 | 91 | 75 | 77 |
| 2 | 90 | 55 | 15 |
| 8 | 96 | 9 | 50 |
| 11 | 52 | 11 | 22 |
| 12 | 43 | 12 | 46 |
| 13 | 60 | 11 | 42 |
| 15 | 56 | 12 | 47 |
| 17 | 105 | 66 | 82 |
| 18 | 74 | 12 | 39 |
| 19 | 89 | 18 | 46 |
| 20 | 58 | 31 | 37 |
| 21 | 106 | 66 | 78 |
| 23 | 98 | 51 | 50 |

It was revealed from the results shown in Table 4 that the recording materials of the present invention are good in the image heat resistance, the plasticizer resistance and the alcohol resistance.

The invention claimed is:

1. A recording material containing a color former and at least one compound selected from the group consisting of compounds represented by the following formula (I):

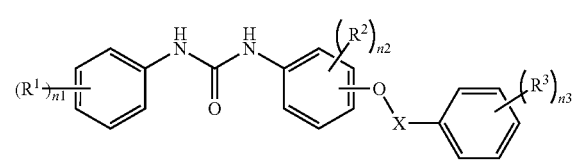

wherein:

X represents $CH_2$, $C{=}O$, or $SO_2$;

$R^1$ to $R^3$ each independently represent a hydrogen atom, a halogen atom, a nitro group, a cyano group, a linear, branched or cyclic C1-C6 alkylcarbonyl group, a linear, branched or cyclic C1-C6 alkyl group, a linear, branched or cyclic C1-C6 alkoxy group, a C2-C6 alkenyl group, a linear, branched or cyclic C1-C6 fluoroalkyl group, a $N(R^4)_2$ group, wherein $R^4$ represents a hydrogen atom, a phenyl group, a benzyl group, or a linear, branched or cyclic C1-C6 alkyl group, a $NHCOR^5$ group, wherein $R^5$ represents a linear, branched or cyclic C1-C6 alkyl group, an optionally substituted phenyl group, or an optionally substituted benzyl group;

n1 and n3 each independently represent any integer of 1 to 5;

two groups represented by $R^3$ adjacent to each other on a benzene ring optionally bond to each other to form an optionally substituted 6-membered ring;

n2 represents any integer of 1 to 4; and when X is $SO_2$, at least one $R^1$ and/or at least one $R^2$ is not a hydrogen atom.

2. A recording sheet having a recording material layer formed with the recording material according to claim 1 on a support.

* * * * *